(12) United States Patent
Newcombe et al.

(10) Patent No.: US 7,485,638 B2
(45) Date of Patent: Feb. 3, 2009

(54) PYRIMIDINE COMPOUNDS

(75) Inventors: Nicholas John Newcombe, Macclesfield (GB); Andrew Peter Thomas, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 567 days.

(21) Appl. No.: 10/507,162

(22) PCT Filed: Mar. 6, 2003

(86) PCT No.: PCT/GB03/00957

§ 371 (c)(1),
(2), (4) Date: Sep. 9, 2004

(87) PCT Pub. No.: WO03/076435

PCT Pub. Date: Sep. 18, 2003

(65) Prior Publication Data

US 2005/0256311 A1 Nov. 17, 2005

(30) Foreign Application Priority Data

Mar. 9, 2002 (GB) .................................. 0205688.5

(51) Int. Cl.
C07D 403/04 (2006.01)
A61K 31/506 (2006.01)

(52) U.S. Cl. .............................. 514/235.8; 514/255.05; 514/275; 544/122; 544/331

(58) Field of Classification Search ................. 544/122, 544/331; 514/235.8, 255.05, 275
See application file for complete search history.

(56) References Cited

U.S. PATENT DOCUMENTS

| 4,983,608 | A | 1/1991 | Effland et al. |
| 5,516,775 | A | 5/1996 | Zimmermann et al. |
| 5,521,184 | A | 5/1996 | Zimmermann |
| 5,610,303 | A | 3/1997 | Kimura et al. |
| 5,739,143 | A | 4/1998 | Adams et al. |
| 5,859,041 | A | 1/1999 | Liverton et al. |
| 6,593,326 | B1 | 7/2003 | Bradbury et al. |
| 6,632,820 | B1 | 10/2003 | Breault et al. |
| 6,649,608 | B2 | 11/2003 | Pease et al. |
| 6,670,368 | B1 | 12/2003 | Breault et al. |
| 6,710,052 | B2 | 3/2004 | Pease et al. |
| 6,716,831 | B1 | 4/2004 | Breault et al. |
| 6,835,726 | B2 | 12/2004 | Cushing et al. |
| 6,838,464 | B2 | 1/2005 | Pease et al. |
| 6,844,341 | B2 | 1/2005 | Thomas |
| 6,855,719 | B1 | 2/2005 | Thomas et al. |
| 6,906,065 | B2 | 6/2005 | Thomas |
| 6,908,920 | B2 | 6/2005 | Thomas et al. |
| 6,939,872 | B2 | 9/2005 | Newcombe et al. |
| 6,969,714 | B2 * | 11/2005 | Breault et al. ............ 514/235.8 |
| 7,067,522 | B2 | 6/2006 | Pease et al. |
| 7,153,964 | B2 | 12/2006 | Pease et al. |
| 7,176,212 | B2 | 2/2007 | Breault et al. |
| 2003/0144303 | A1 | 7/2003 | Hawley et al. |
| 2003/0191307 | A1 | 10/2003 | Blumenkopf et al. |
| 2004/0102630 | A1 | 5/2004 | Brumby et al. |
| 2004/0224966 | A1 | 11/2004 | Brumby et al. |
| 2005/0176743 | A1 | 8/2005 | Luecking et al. |
| 2006/0079543 | A1 | 4/2006 | Sum et al. |
| 2006/0111378 | A1 | 5/2006 | Cleve et al. |

FOREIGN PATENT DOCUMENTS

| CA | 2231765 | 9/1998 |
| EP | 0 135 472 | 3/1985 |
| EP | 0 363 002 | 4/1990 |
| EP | 0 379 806 B1 | 8/1990 |
| EP | 0 945 443 A1 | 9/1999 |
| EP | 1056742 | 7/2003 |
| HU | 220630 | 3/2002 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |
| WO | 96/05177 | 2/1996 |
| WO | 96/28427 | 9/1996 |
| WO | 96/40143 | 12/1996 |
| WO | 97/19065 | 5/1997 |
| WO | 97/35856 | 10/1997 |

(Continued)

OTHER PUBLICATIONS

Traxler, Protein tyrosine kinase inhibitors in cancer treatment, Expert Opinion on Therapeutic Patents, 7(6), pp. 571-588, 1997.*

(Continued)

*Primary Examiner*—Deepak Rao
(74) *Attorney, Agent, or Firm*—Morgan, Lewis & Bockius LLP

(57) ABSTRACT

Compounds of the formula (I), wherein $R^1$, $R^2$, $R^3$, $R^4$, $R^5$ and p are as defined within and a pharmaceutically acceptable salts and in vivo hydrolysable esters are described. Also described are processes for their preparation and their use as medicaments, particularly medicaments for producing a cell cycle inhibitory (anti-cell-proliferation) effect in a warm-blooded animal, such as man.

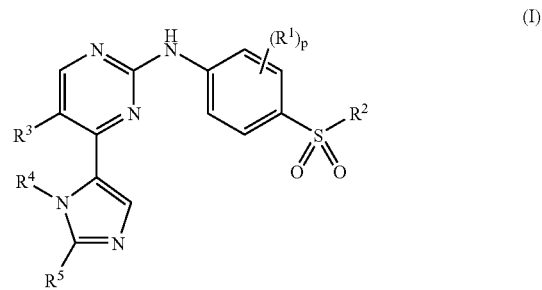

(I)

12 Claims, No Drawings

FOREIGN PATENT DOCUMENTS

| | | |
|---|---|---|
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 | 8/1998 |
| WO | 98/41512 | 9/1998 |
| WO | 98/54093 | 12/1998 |
| WO | 98/56788 | 12/1998 |
| WO | 99/01136 | 1/1999 |
| WO | 99/32121 | 1/1999 |
| WO | 99/18096 | 4/1999 |
| WO | 99/18942 | 4/1999 |
| WO | 99/31073 | 6/1999 |
| WO | 99/41253 | 8/1999 |
| WO | 99/50250 | 10/1999 |
| WO | 99/50251 | 10/1999 |
| WO | 00/12485 | 3/2000 |
| WO | 00/12486 | 3/2000 |
| WO | 00/17202 | 3/2000 |
| WO | 00/17203 | 3/2000 |
| WO | 00/21926 | 4/2000 |
| WO | 00/25780 | 5/2000 |
| WO | 00/26209 | 5/2000 |
| WO | 00/39101 | 6/2000 |
| WO | 00/44750 | 8/2000 |
| WO | 00/49018 | 8/2000 |
| WO | 00/53595 | 9/2000 |
| WO | 00/55161 | 9/2000 |
| WO | 00/59892 | 10/2000 |
| WO | 00/78731 A1 | 12/2000 |
| WO | 01/14375 A | 3/2001 |
| WO | WO 01/14375 | 3/2001 |
| WO | 01/29009 A1 | 4/2001 |
| WO | 01/30778 A1 | 5/2001 |
| WO | 01/37835 A1 | 5/2001 |
| WO | 01/47897 A1 | 7/2001 |
| WO | 01/47921 A1 | 7/2001 |
| WO | 01/60816 A1 | 8/2001 |
| WO | 01/64653 A1 | 9/2001 |
| WO | 01/64654 A1 | 9/2001 |
| WO | 01/64655 A1 | 9/2001 |
| WO | 01/64656 A1 | 9/2001 |
| WO | 01/72717 A1 | 10/2001 |
| WO | 02/04429 A1 | 1/2002 |
| WO | 02/20512 A | 3/2002 |
| WO | WO 02/20512 | 3/2002 |
| WO | WO 02/46170 | 6/2002 |
| WO | WO 02/46171 | 6/2002 |
| WO | 02/066481 A1 | 8/2002 |
| WO | WO 02/065979 | 8/2002 |
| WO | WO 02/066480 | 8/2002 |
| WO | WO 02/092573 | 11/2002 |
| WO | 02/096887 A1 | 12/2002 |
| WO | WO 02/096888 | 12/2002 |
| WO | 03/007955 A2 | 1/2003 |
| WO | WO 03/011837 | 2/2003 |
| WO | WO 03/029249 | 4/2003 |
| WO | WO 03/031446 | 4/2003 |
| WO | WO 03/037891 | 5/2003 |
| WO | 03/076433 A1 | 9/2003 |
| WO | 03/076434 A1 | 9/2003 |
| WO | 03/076436 A1 | 9/2003 |
| WO | WO 2004/005283 | 1/2004 |
| WO | WO 04/043953 | 5/2004 |
| WO | WO 2004/043467 | 5/2004 |
| WO | WO 2004/087698 | 10/2004 |
| WO | WO 2004/087699 | 10/2004 |
| WO | WO 2004/101549 | 11/2004 |
| WO | WO 2004/101564 | 11/2004 |
| WO | WO 2005/012298 | 2/2005 |
| WO | WO 2005/037800 | 4/2005 |
| WO | WO 2005/075461 | 8/2005 |
| WO | WO 2005/075468 | 8/2005 |
| WO | WO 2005/113550 | 12/2005 |
| WO | WO 2005/116025 | 12/2005 |
| WO | WO 2006/034872 | 4/2006 |
| WO | WO 2006/044509 | 4/2006 |
| WO | WO 2006/050076 | 5/2006 |
| WO | WO 2006/064251 | 6/2006 |
| WO | WO 2006/075152 | 7/2006 |
| WO | WO 2006/095159 | 9/2006 |
| WO | WO 2007/015064 | 2/2007 |
| WO | WO 2007/036732 | 4/2007 |
| WO | WO 2007/040440 | 4/2007 |

OTHER PUBLICATIONS

Lu Valle et al., Cell Cycle Control in Growth Plate Chondrocytes, Frontiers in Bioscience 5, d493-503, May 2000.*

Boschelli et al., Synthesis and Tyrosine Kinase Inhibitory Activity of a Series of 2-Amino-8-H-pyrido[2,3-d]pyrimidines: Identification of Potent, Selective Platelet-Derived Growth Factor Receptor Tyrosine Kinase Inhibitors, J. Med. Chem., vol. 41, 1998, pp. 4365-4377.

Deady et al., "Reactions of some Quinazoline Compounds with Ethoxymethylenemalonic Acid Derivatives", J. Heterocyclic Chem., vol. 26, 1989, pp. 161-168.

El-Kerdawy et al.; "2,4-Bis (Substituted)-5-Nitropyrimidines of Expected Diuretic Action"; Egypt J. Chem. vol. 29, No. 2, 1986, pp. 247-251.

Fiziol Akt Veshchestva, 1975, vol. 7, pp. 68-72.

Ghosh et al.; "2,4-Bis(arylamino)-5-methylpyrimidines as Antimicrobial Agents"; J. Med. Chem., 1967, vol. 10, No. 5, pp. 974-975.

Ghosh, "2,4-Bis(Arylamino)-6-Methyl Pyrimidines as Antimicrobial Agents", J. Indian Chem. Soc., vol. 58, No. 5, 1981, pp. 512-513.

Schmidt et al.; "A Convenient Synthesis of 2-substituted 4-Amino-5-pyrimidinecarbonitriles"; J. Heterocycle Chem., 1997, vol. 24, No. 5, pp. 1305-1307.

Zimmermann et al., Phenylamino-Pyrimidine (PAP) Derivatives: A New Class of Potent and Selective Inhibitors of Protein Kinase C (PKC), Arch. Pharm. Pharm. Med. Chem., vol. 329, 1996, pp. 371-376.

Blain et al. "Differential Interaction of the Cyclin-dependent Kinase (Cdk) Inhibitor p27Kip1 with Cyclin A-Cdk2 and Cyclin D2-Cdk4" J. Biol. Chem. 272(41): 25863-25872 (1997).

Simone, Oncology: Introduction, Cecil Textbook of Medicine, 20th Edition, vol. 1, pp. 1004-1010 (1996).

Volin et al. "Cell cycle implications in the pathogenesis of rheumatoid arthritis" Frontiers in Bioscience 5:D594-601(2000).

Fiziol Akt Veshchestva 7:68-72 (1975) (Translation enclosed).

* cited by examiner

PYRIMIDINE COMPOUNDS

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases: (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of formula (I):

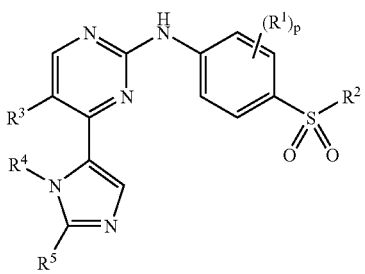

(I)

wherein:
$R^1$ is halo, cyano, $C_{1-3}$alkyl or $C_{1-3}$alkoxy;
p is 0-2; wherein the values of $R^1$ may be the same or different;
$R^2$ is amino, $R^6$ or $R^6$—NH;
$R^3$ is hydrogen, halo or cyano;
$R^4$ is $C_{3-6}$cycloalkyl, $C_{3-6}$cycloalkyl$C_{1-4}$alkyl, benzyl, heterocyclyl, heterocyclyl$C_{1-4}$alkyl or 1-methoxyprop-2-yl; wherein $R^4$ may be optionally substituted on ring carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen mnay be optionally substituted by one or more methyl, ethyl, acetyl, 2,2,2-trifluoroethyl or methoxyethyl;
$R^5$ is $C_{1-6}$alkyl or $C_{2-6}$alkenyl; wherein $R^5$ may be optionally substituted on carbon by one or more methoxy, ethoxy, propoxy, trifluoromethyl, trifluoromethoxy, 2,2,2-trifluoroethoxy or cyclopropylmethoxy;
$R^6$ is $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclic group or (heterocyclic group)$C_{1-3}$alkyl; wherein $R^6$ may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclic group contains an —NH— moiety that nitrogen may be optionally substituted by one or more methyl, ethyl, acetyl, 2,2,2-trifluoroethyl or methoxyethyl;

or a pharmaceutically acceptable salt or an in vivo hydrolysable ester thereof.

According to a further aspect of the present invention provides a compound of formula (I) (as depicted above) wherein:
$R^1$ is halo, cyano, $C_{1-3}$alkyl or $C_{1-3}$alkoxy;
p is 0-2; wherein the values of $R^1$ may be the same or different;
p is 0-2; wherein the values of $R^1$ may be the same or different;
$R^2$ is amino, $R^6$ or $R^6$—NH;
$R^3$ is hydrogen, halo or cyano;
$R^4$ is $C_{3-6}$cycloalkyl, $C_{3-6}$cycloalkyl$C_{1-4}$alkyl, heterocyclyl, heterocyclyl$C_{1-4}$alkyl or 1-methoxyprop-2-yl; wherein $R^4$ may be optionally substituted on ring carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen mnay be optionally substituted by one or more methyl, ethyl, acetyl, 2,2,2-trifluoroethyl or methoxyethyl;
$R^5$ is $C_{1-6}$alkyl or $C_{2-6}$alkenyl; wherein $R^5$ may be optionally substituted on carbon by one or more methoxy, ethoxy, propoxy, trifluoromethyl, trifluoromethoxy, 2,2,2-trifluoroethoxy or cyclopropylmethoxy;
$R^6$ is $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclic group or (heterocyclic group)$C_{1-3}$alkyl; wherein $R^6$ may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclic group contains an —NH— moiety that nitrogen may be optionally substituted by one or more methyl, ethyl, acetyl, 2,2,2-trifluoroethyl or methoxyethyl;

or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl", "$C_{1-4}$alkyl" and "$C_{1-3}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "$C_{3-6}$cycloalkyl$C_{1-4}$alkyl" and "$C_{3-6}$cycloalkyl$C_{1-3}$alkyl" includes cyclopropylmethyl, 1-cyclobutylethyl and 3-cyclopropylpropyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated monocyclic ring, linked via a ring carbon, which contains 3-6 atoms of which at least one atom is chosen from nitrogen, sulphur or oxygen and a ring sulphur atom may be optionally oxidised to form the S-oxide(s). Examples and suitable values of the term "heterocyclyl" are tetrahydrofuranyl, pyrrolidinyl, dioxolanyl, pyrazolidinyl, piperidinyl, dioxanyl, morpholinyl, thiomorpholinyl or 1,1-dioxothiomorpholino. Suitably "heterocyclyl" is tetrahydrofuranyl.

A "heterocyclic group" is a saturated, partially saturated or unsaturated, monocyclic ring containing 4-6 atoms of which at least one atom is chosen from nitrogen, sulphur or oxygen, which may, unless otherwise specified, be carbon or nitrogen linked, and a ring sulphur atom may be optionally oxidised to form the S-oxide(s). Examples and suitable values of the term "heterocyclic group" are morpholino, piperidyl, pyridyl, pyranyl, pyrrolyl, isothiazolyl, thienyl, thiadiazolyl, piperazinyl, thiazolidinyl, thiomorpholino, pyrrolinyl, tetrahydropyranyl, tetrahydrofuryl, imidazolyl, pyrimidyl, pyrazinyl, pyridazinyl and isoxazolyl. Suitably a "heterocyclic group" is pyridyl.

Examples of "$C_{1-3}$alkoxy" include, methoxy, ethoxy and propoxy. Examples of "$C_{2-6}$alkenyl" and "$C_{2-4}$alkenyl" are vinyl, allyl, 2-methylprop-1-enyl and 1-propenyl. Examples of "$C_{2-4}$alkynyl" are ethynyl, 1-propynyl and 2-propynyl. Examples of "$C_{3-6}$cycloalkyl" are cyclopropyl, cyclobutyl, cyclopentyl and cyclohexyl. Examples of "(heterocyclic group)$C_{1-3}$alkyl" include pyridylmethyl, 3-morpholinopropyl and 2-pyrimid-2-ylethyl. Examples of "heterocyclyl$C_{1-6}$alkyl" are tetrahydrofurylmethyl, 2-morpholinoethyl and 2-pyrrolidin-1-ylpropyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4- position of the benzoyl ring.

Some compounds of the formula (I) may have chiral centres and/or geometric isomeric centres (E- and Z- isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity. In particular the skilled reader will appreciate that when $R^4$ is hydrogen, the imidazole ring as drawn in formula (I) may tautomerise.

It is also to be understood that certain compounds of the formula (I) can exist in solvated as well as unsolvated forms such as, for example, hydrated forms. It is to be understood that the invention encompasses all such solvated forms which possess CDK inhibitory activity.

Suitable values of $R^1$, $R^2$, $R^3$, $R^4$, $R^5$ and p are as follows. Such values may be used where appropriate with any of the definitions, claims or embodiments defined hereinbefore or hereinafter. $R^1$ is fluoro, chloro, cyano, methyl, ethyl, methoxy or ethoxy.

p is 0.

p is 1.

p is 2.

$R^2$ is $R^6$—NH— wherein $R^6$ is $C_{1-4}$alkyl, $C_{2-4}$alkenyl, $C_{3-6}$cycloalkyl, $C_{3-6}$cycloalkyl$C_{1-3}$alkyl or (heterocyclic group)$C_{1-3}$alkyl; and wherein $R^6$ may be optionally substituted on carbon by one methoxy, ethoxy or trifluoromethyl.

$R^2$ is $R^6$—NH— wherein $R^6$ is $C_{1-4}$alkyl, $C_{2-4}$alkenyl, $C_{3-6}$cycloalkyl, $C_{3-6}$cycloalkyl$C_{1-3}$alkyl or (heterocyclic group)$C_{1-3}$alkyl; and wherein $R^6$ may be optionally substituted on carbon by one methyl, methoxy, ethoxy or trifluoromethyl.

$R^2$ is $R^6$—NH— wherein $R^6$ is methyl, ethyl, propyl, t-butyl, allyl, cyclopropyl, cyclobutyl, cyclopropylmethyl, tetrahydrofur-2-ylmethyl or pyrid-2-ylmethyl; and wherein $R^6$ may be optionally substituted on carbon by one methoxy, ethoxy or trifluoromethyl.

$R^2$ is $R^6$—NH— wherein $R^6$ is methyl, ethyl, propyl, t-butyl, allyl, cyclopropyl, cyclobutyl, cyclopropylmethyl, tetrahydrofur-2-ylmethyl or pyrid-2-ylmethyl; and wherein $R^6$ may be optionally substituted on carbon by one methyl, methoxy, ethoxy or trifluoromethyl.

R² is methylamino, allylamino, t-butylamino, 2-methoxyethylamino, 2-ethoxyethylamino, 3-methoxypropylamino, cyclopropylamino, cyclobutylamino, cyclopropylmethylamino, 2,2,2-trifluoroethylamino, tetrahydrofur-2-ylmethylamino or pyrid-2-ylmethylamino.

R³ is hydrogen, chloro or fluoro.

R³ is hydrogen.

R⁴ is $C_{3-6}$cycloalkyl, $C_{3-6}$cycloalkyl$C_{1-4}$alkyl, heterocyclyl or 1-methoxyprop-2-yl.

R⁴ is $C_{3-6}$cycloalkyl, $C_{3-6}$cycloalkyl$C_{1-4}$alkyl, benzyl, heterocyclyl or 1-methoxyprop-2-yl.

R⁴ is cyclopropylmethyl, cyclobutyl, cyclopropyl, cyclopentyl, 1-methoxyprop-2-yl or tetrahydrofuryl.

R⁴ is cyclopropylmethyl, 2-cyclopropylethyl, cyclobutyl, cyclopropyl, cyclopentyl, benzyl, 1-methoxyprop-2-yl or tetrahydrofuryl.

R⁴ is cyclopropylmethyl, cyclobutyl, cyclopropyl, cyclopentyl, 1-methoxyprop-2-yl or tetrahydrofur-3-yl.

R⁴ is cyclopropylmethyl, 2-cyclopropylethyl, cyclobutyl, cyclopropyl, cyclopentyl, benzyl, 1-methoxyprop-2-yl or tetrahydrofur-3-yl.

R⁵ is $C_{1-6}$alkyl.

R⁵ is $C_{1-3}$alkyl.

R⁵ is methyl.

R⁵ is $C_{1-6}$alkyl or $C_{2-6}$alkenyl; wherein R⁵ may be optionally substituted on carbon by one or more methoxy.

R⁵ is methyl, ethyl, propyl or 2-methylprop-1-enyl; wherein R⁵ may be optionally substituted on carbon by one or more methoxy.

R⁵ is methyl, ethyl, propyl, methoxymethyl or 2-methylprop-1-enyl.

Therefore in another aspect of the invention, there is provided a compound of formula (I) (as depicted above) wherein:

p is 0;

R² is R⁶—NH— wherein R⁶ is $C_{1-4}$alkyl, $C_{2-4}$alkenyl, $C_{3-6}$cycloalkyl, $C_{3-6}$cycloalkyl$C_{1-3}$alkyl or (heterocyclic group)$C_{1-3}$alkyl; and wherein R⁶ may be optionally substituted on carbon by one methoxy, ethoxy or trifluoromethyl;

R³ is hydrogen;

R⁴ is $C_{3-6}$cycloalkyl, $C_{3-6}$cycloalkyl$C_{1-4}$alkyl, heterocyclyl or 1-methoxyprop-2-yl;

R⁵ is $C_{1-6}$alkyl;

or a pharmaceutically acceptable salt or an in vivo hydrolysable ester thereof.

Therefore in another aspect of the invention, there is provided a compound of formula (I) (as depicted above) wherein:

p is 0;

R² is R⁶—NH— wherein R⁶ is $C_{1-4}$alkyl, $C_{2-4}$alkenyl, $C_{3-6}$cycloalkyl, $C_{3-6}$cycloalkyl$C_{1-3}$alkyl or (heterocyclic group)$C_{1-3}$alkyl; and wherein R⁶ may be optionally substituted on carbon by one methoxy, ethoxy or trifluoromethyl;

R³ is hydrogen;

R⁴ is $C_{3-6}$cycloalkyl, $C_{3-6}$cycloalkyl$C_{1-4}$alkyl, benzyl, heterocyclyl or 1-methoxyprop-2-yl;

R⁵ is $C_{1-6}$alkyl or $C_{2-6}$alkenyl; wherein R⁵ may be optionally substituted on carbon by one or more methoxy;

or a pharmaceutically acceptable salt or an in vivo hydrolysable ester thereof.

Therefore in an additional aspect of the invention, there is provided a compound of formula (I) (as depicted above) wherein:

p is 0;

R² is methylamino, allylamino, t-butylamino, 2-methoxyethylamino, 2-ethoxyethylamino, 3-methoxypropylamino, cyclopropyl amino, cyclobutyl amino, cyclopropylmethylamino, 2,2,2-trifluoroethylamino, tetrahydrofur-2-ylmethylamino or pyrid-2-ylmethylamino;

R³ is hydrogen;

R⁴ is cyclopropylmethyl, cyclobutyl, cyclopropyl, cyclopentyl, 1-methoxyprop-2-yl, or tetrahydrofur-3-yl;

R⁵ is methyl;

or a pharmaceutically acceptable salt or an in vivo hydrolysable ester thereof.

Therefore in an additional aspect of the invention, there is provided a compound of formula (I) (as depicted above) wherein:

p is 0;

R² is methylamino, allylamino, t-butylamino, 2-methoxyethylamino, 2-ethoxyethylamino, 3-methoxypropylamino, cyclopropylamino, cyclobutylamino, cyclopropylmethylamino, 2,2,2-trifluoroethylamino, tetrahydrofur-2-ylmethylamino or pyrid-2-ylmethylamino;

R³ is hydrogen;

R⁴ is cyclopropylmethyl, 2-cyclopropylethyl, cyclobutyl, cyclopropyl, cyclopentyl, benzyl, 1-methoxyprop-2-yl or tetrahydrofur-3-yl;

R⁵ is methyl, ethyl, propyl, methoxymethyl or 2-methylprop-1-enyl;

or a pharmaceutically acceptable salt or an in vivo hydrolysable ester thereof.

In another aspect of the invention, particular compounds of the invention are any one of the Examples or a pharmaceutically acceptable salt or an in vivo hydrolysable ester thereof.

In another aspect of the invention, particular compounds of the invention are any one of Examples 7, 22, 23, 24, 25, 34, 39, 41, 46 or 48 or a pharmaceutically acceptable salt or an in vivo hydrolysable ester thereof.

A particular aspect of the invention is that which relates to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein R¹, R², R³, R⁴, R⁵ and p are, unless otherwise specified, as defined in formula (I)) comprises of:

Process a) reaction of a pyrimidine of formula (II):

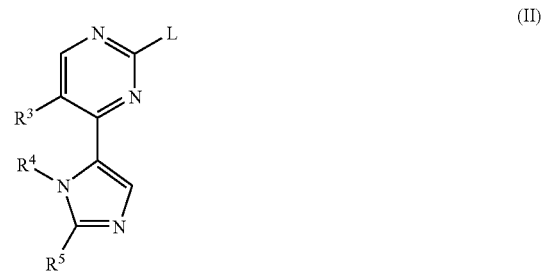

(II)

wherein L is a displaceable group; with an aniline of formula (III):

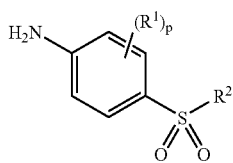
(III)

or

Process b) reacting a compound of formula (IV):

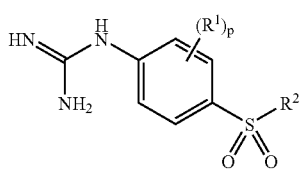
(IV)

with a compound of formula (V):

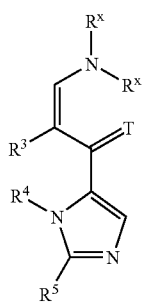
(V)

wherein T is O or S; $R^x$ may be the same or different and is $C_{1-6}$alkyl;

Process c) for compounds of formula (I) where $R^2$ is amino or a group $R^6$ —NH—; reacting a pyrimidine of formula (VI):
(VI)

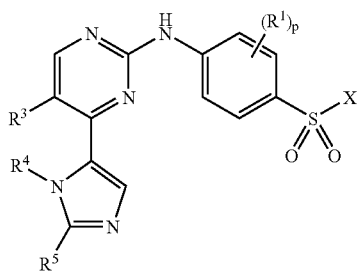

wherein X is a displaceable group; with an amine of formula (VII):

$R^a$—NH$_2$ (VII)

wherein Ra is hydrogen or $R^6$;

Process d) reacting a pyrimidine of formula (VIII)

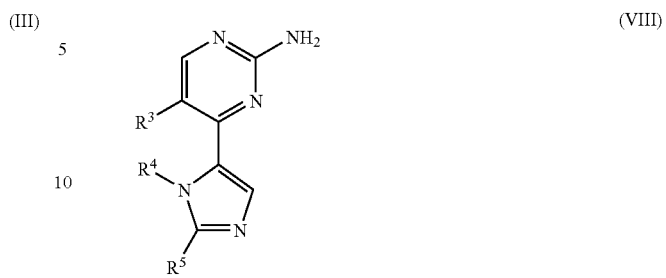
(VIII)

with a compound of formula (IX):

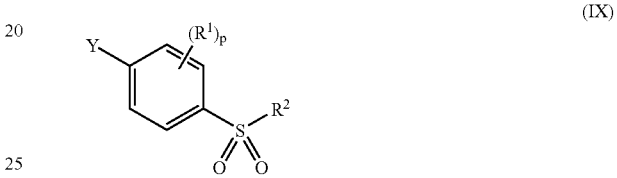
(IX)

where Y is a displaceable group; or

Process e) for compounds of formula (I) wherein $R^2$ is $R^6$; oxidising a compound of formula (X):

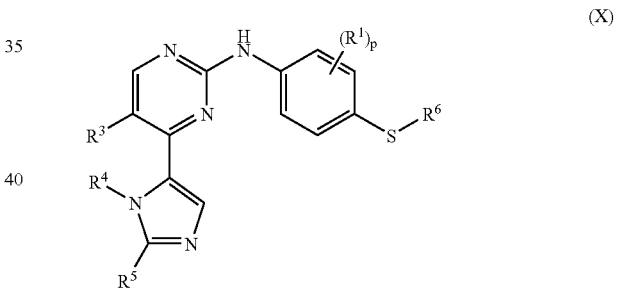
(X)

and thereafter if necessary:
　i) converting a compound of the formula (I) into another compound of the formula (I);
　ii) removing any protecting groups;
　iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

X is a displaceable group, suitable values for X are for example, a fluoro or chloro group. Preferably X is fluoro.

Y is a displaceable group, suitable values for Y are for example, a halogeno or sulphonyloxy group, for example a bromo, iodo or trifluoromethanesulphonyloxy group. Preferably Y is iodo.

Specific reaction conditions for the above reactions are as follows.

Process a) Pyrimidines of formula (II) and anilines of formula (III) may be reacted together:

i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) where L is chloro may be prepared according to Scheme 1:

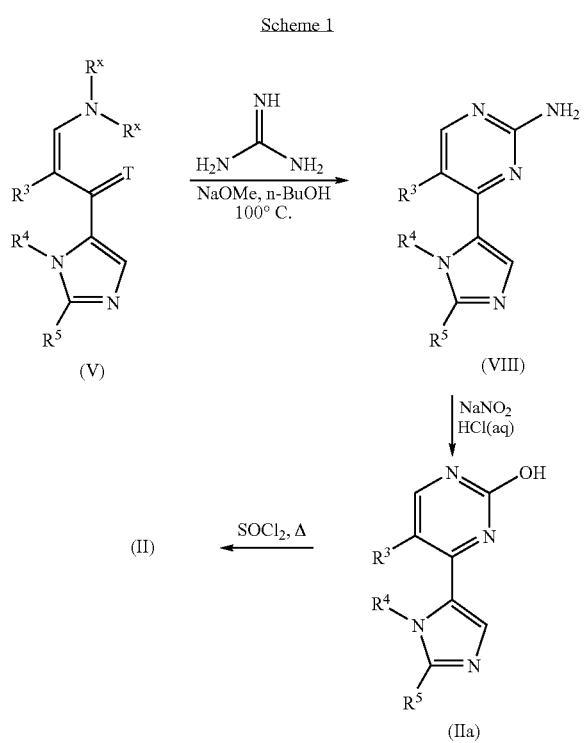

Anilines of formula (III) are commercially available compounds, or they are known in the literature, or they are prepared by standard processes known in the art.

Process b) Compounds of formula (IV) and compounds of formula (V) are reacted together in a suitable solvent such as N-methylpyrrolidinone or butanol at a temperature in the range of 100-200° C., preferably in the range of 150-170° C. The reaction is preferably conducted in the presence of a suitable base such as, for example, sodium hydride, sodium methoxide or potassium carbonate.

Compounds of formula (V) may be prepared according to Scheme 2:

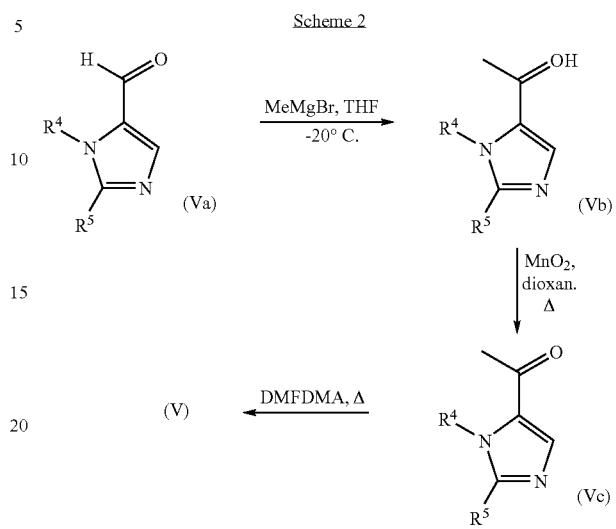

Compounds of formula (IV) and (Va) are commercially available compounds, or they are known in the literature, or they are prepared by standard processes known in the art.

Process c) Compounds of formula (VI) and amines of formula (VII) may be reacted together in the presence of an inert solvent such as N-methylpyrrolidinone or pyridine, in the presence of a base for example an inorganic base such as caesium carbonate or in the presence of an organic base such as excess (VII) and at a temperature in the range of 25 to 80° C.

Compounds of formula (VI) (wherein X is chloro) may be prepared according to Scheme 3:

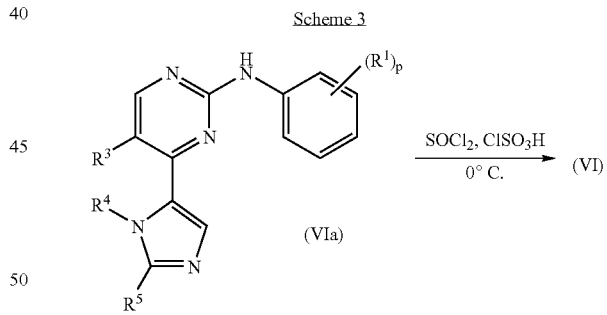

Compounds of formula (VIa) may be prepared according to Process a, Process b or Process d but wherein compounds (III), (IV) and (IX) are not substituted by $R^2SO_2$—.

Process d) Compounds of formula (VIII) and amines of formula (IX) may be reacted together under standard Buchwald conditions as described in Process a.

The synthesis of compounds of formula (VIII) is described in Scheme 1.

Compounds of formula (IX) are commercially available compounds, or they are known in the literature, or they are prepared by standard processes known in the art.

Amines of formula (VI) are commercially available compounds, or they are known in the literature, or they are prepared by standard processes known in the art.

Process e) Compounds of formula (X) may be oxidised under standard sulphur oxidation conditions; for example using hydrogen peroxide and trifluoroacetic acid at a temperature, or oxone in methanol and acetone; or titanium isopropoxide and cumene hydroperoxide in butyl acetate; preferably at or near room temperature.

Compounds of formula (X) may be prepared using a process described above for the preparation of a compound of formula (I) but wherein the sulphone of formula (I) is a sulphide.

In one aspect of the invention, there is provided a process for preparing a compound of formula (I) which is a process selected from Process a), Process b), Process c) or Process d).

In another aspect of the invention, there is provided a process for preparing a compound of formula (I) which is Process e).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedures set out in WO 02/04429.

Although the pharmacological properties of the compounds of the formula (I) vary with structural change, in general activity possessed by compounds of the formula (I) may be demonstrated at $IC_{50}$ concentrations or doses in the range 250 μM to 1 nM in the in vitro assay described in WO 02/04429.

Typical $IC_{50}$ values for compounds of the invention when tested in the SRB assay described in WO 02/04429 are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin. Particularly "cancer" is selected from leukaemia, breast cancer, lung cancer, colorectal cancer, stomach cancer, prostate cancer, bladder cancer, pancreatic cancer, ovarian cancer, liver cancer, kidney cancer, skin cancer and cancer of the vulva.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2, CDK4 and/or CDK6, especially CDK2.

According to a further feature of the invention, there is provided a compound of the formula (I), or a pharmaceutically acceptable salt or in vivo hydrolysable ester thereof, as defined herein before in the manufacture of a medicament for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK2, CDK4 and/or CDK6, especially CDK2.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of formula (I) or a pharmaceutically acceptable salt or in vivo hydrolysable ester thereof as defined herein before. Particularly, an inhibitory effect is produced by preventing entry into or progression through the S phase by inhibition of CDK2, CDK4 and/or CDK6, especially CDK2.

According to an additional feature of this aspect of the invention there is provided a method of treating cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal, such as man, in need of such treatment which comprises administering to said animal an effective amount of a compound of formula (I) or a pharmaceutically acceptable salt or in vivo hydrolysable ester thereof as defined herein before.

Particularly there is provided a method of treating cancer in a warm-blooded animal, such as man, in need of such treatment which comprises administering to said animal an effective amount of a compound of formula (I) or a pharmaceutically acceptable salt or in vivo hydrolysable ester thereof as defined herein before.

In a further aspect of the invention there is.provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the production of a cell cycle inhibitory (anti-cell-proliferation) effect in a warmn-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancer in a warm-blooded animal such as man.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK2 or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophosphamide; anti metabolites such as methotrexate, 5-fluorouracil, gemcitabine and cytarabine; vinca alkaloids and analogues such as vincristine, vinbalstine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use in preventing hair loss arising from the treatment of malignant conditions with pharmaceutical agents which comprises a compound of formula (I), or a pharmaceutically acceptable salt or in vivo hydrolysable ester thereof, and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a further aspect of the present invention there is provided a kit comprising:
a) a compound of formula (I), or a pharmaceutically acceptable salt or in vivo hydrolysable ester thereof, in a first unit dosage form;
b) a pharmaceutical agent for treating malignant conditions that is known to cause hair loss; in a second unit dosage form; and
c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore maybe: surgery, radiotherapy or chemotherapy. Such chemotherapy may cover three main categories of therapeutic agent:
(i) other cell cycle inhibitory agents that work by the same or different mechanisms from those defined hereinbefore;
(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

Some of the intermediates described herein are novel and are thus provided as a further aspect of the invention. For example, an additional aspect of the invention refers to a compound of formula (X).

EXAMPLES

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(MH)^+$;

(xi) unless stated otherwise compounds containing an asymmetricallysubstituted carbon and/or sulphur atom have not been resolved;

(xii) where a synthesis is described as being analogous to that described in a previous example the amounts used are the millimolar ratio equivalents to those used in the previous example;

(xvi) the following abbreviations have been used:

| | |
|---|---|
| EtOAc | ethyl acetate; |
| ether | diethyl ether; |
| MeOH | methanol; and |
| DCM | dichloromethane; | xvii) where an Isolute SCX-2 column is referred to, this means an "ion exchange" extraction cartridge for adsorption of basic compounds, i.e. a polypropylene tube containing a benzenesulphonic acid based strong cation exchange sorbent, used according to the manufacturers instructions obtained from International Sorbent Technologies Limited, Dyffryn Business Park, Hengeod, Mid Glamorgan, UK, CF82 7RJ;

xviii) where an Isolute amine column is referred to, this means an "ion exchange" extraction cartridge for adsorption of acidic compounds, i.e. a polypropylene tube containing a amino silane covalently bonded to a silica particle used according to the manufacturers instructions obtained from International Sorbent Technologies Limited, Dyffryn Business Park, Hengeod, Mid Glamorgan, UK, CF82 7RJ;

Example 1

4-(1-Cyclobutyl-2-methylimidazol-5-yl)-2-{4-[N-(cyploroylmethyl)sulphamoyl]anilino}pyrimidine Chlorosulphonic acid (150 μl, 2.16 mmol) was added dropwise to solution of 2-anilino-4-(1-cyclobutyl-2-methylimidazol-5-yl)pyrimidine (Method 61; 165 mg, 0.54 mmol) in thionyl chloride (3 ml), cooled to 0° C. and the mixture stirred at 0° C. for 10 minutes then heated at 90° C. for 90 minutes. The volatiles were removed by evaporation and the residue was dried under high vacuum (<2 mmHg) for 1 hour. The resulting solid was placed under nitrogen and a solution of cyclopropylmethylamine (700 μl, 8.1 mmol) in MeOH (3 ml) added. The mixture was stirred for 30 minutes and the volatiles were evaporated in vacuo. Water (20 ml) was added and the precipitated solid was collected by filtration, washed with water (2×10 ml). The solid was dissolved in MeOH and poured onto an Isolute amine column and eluted first with MeOH (30 ml). The solvent was evaporated in vacuo and the resultant foam triturated with ether. The solid was collected by filtration and washed with ether (2×10 ml) and dried under vacuum at 60° C. to yield a beige solid. The solid was slurried in ether (6 ml), 1M HCl in ether (2 ml, 2 mmol) and the solvent evaporated in vacuo. The resultant solid was triturated with ether, collected by filtration and dried in vacuo to yield the title compound (174 mg, 63%) as a hygroscopic solid. NMR: 0.05 (m, 2H), 0.34 (m, 2H), 0.79 (m, 1H), 1.70 (m, 2H), 2.37 (m, 4H), 2.62 (m, 2H), 2.75 (s, 3H), 5.40 (m, 1H), 7.23 (d, 1H), 7.54 (brs, 1H), 7.76 (d, 2H), 7.91 (d, 2H), 8.14 (s, 1H), 8.68 (d, 1H), 10.26 (brs, 1H); m/z 429.

Examples 2-19

The following Examples were prepared by the procedure of Example 1 using the appropriate starting materials.

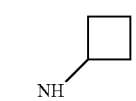

| Ex | Ring A | R$^1$ | NMR | M/z | SM |
|---|---|---|---|---|---|
| 2[1] | cyclobutyl | 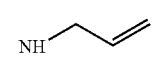 | 1.1-2.12(m, 12H), 5.16(m, 1H), 6.78(d, 1H), 7.06(s, 1H), 7.36(d, 1H), 7.4-7.64(2d, 4H), 8.15(d, 1H), 8.62(s, 1H) | 439 | Meth 61 |
| 3 | cyclobutyl | 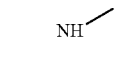 | 1.65(m, 2H), 2.4(m, 4H), 3.39(m, 2H), 4.99(d, 1H), 5.14(d, 1H), 5.48 (m, 1H), 5.66(m, 1H), 7.09(d, 1H), 7.36(s, 1H), 7.58(t, 1H), 7.68(d, 2H), 7.94(d, 2H), 8.46(d, 1H), 9.95 (s, 1H) | 425 | Meth 61 |
| 4 | cyclobutyl | 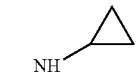 | 1.6(m, 2H), 2.4(m, 6H), 5.5(m, 1H), 5.5(m, 1H), 7.09(d, 1H), 7.2 (m, 1H), 7.36(s, 1H), 7.68(d, 2H), 7.95(d, 2H), 8.45(d, 1H), 9.95(s, 1H) | 399 | Meth 61 |
| 5[1] | cyclobutyl | 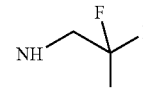 | 1.48, 1.64, 1.72, 1.88, 2.4(5m 10H), 3.57(m, 1H), 5.48(m, 1H), 7.09(d, 1H), 7.36(s, 1H), 7.7(d & s, 3H), 7.9 (m, 2H), 8.45(d, 1H), 9.96(s, 1H) | 425 | Meth 61 |
| 6 | cyclobutyl | 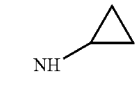 | 1.45-1.9, 2.4, 2.75(m, 12H), 3.5-3.8(m, 3H), 5.48(m, 1H), 7.07(d, 1H), 7.36(s, 1H), 7.46(m, 1H), 7.7-7.94(2d, 4H), 8.45(d, 1H), 9.95(s, 1H) | 469 | Meth 61 |
| 7 | cyclopentyl | 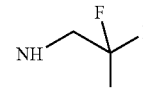 | 0.35(m, 2H), 0.45(m, 2H), 1.53(m, 2H), 1.73(m, 2H), 2.10(m, 5H), 2.77 (s, 3H), 5.55(quin, 1H), 7.25(d, 1H), 7.70(d, 3H), 7.90(d, 2H), 8.18(s, 1H), 8.70(d, 1H), 10.2(s, 1H) | 439 | Meth 62 |
| 8 | cyclobutyl | 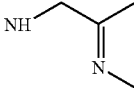 | 1.68(m, 2H), 2.4(m, 4H), 4.04(s, 3H), 5.5(m, 1H), 7.08(d, 1H), 7.2 (m, 1H), 7.37(m, 2H), 7.7(m, 3H), 7.9(d, 2H), 8.4(d, 1H), 8.45(d, 1H), 9.9(s, 1H) | 476 | Meth 61 |

-continued

| Ex | Ring A | R¹ | NMR | M/z | SM |
|---|---|---|---|---|---|
| 9[2] | cyclopentyl | NH-CH₂CH₂-O-CH₃ | 1.54(m, 2H), 1.76(m, 2H), 2.04(m, 2H), 2.19(m, 2H), 2.78(s, 3H), 2.89 (q, 2H), 3.19(s, 3H), 3.32(t, 2H), 5.56(quin, 1H), 7.25(d, 1H), 7.58(t, 1H), 7.73(d, 2H), 7.88(d, 2H), 8.20 (s, 1H), 8.73(d, 1H), 10.20(s, 1H) | 457 | Meth 62 |
| 10 | cyclobutyl | NH-CH₂CH₂CH₂-O-CH₃ | 1.57(m, 2H), 1.71(m, 2H), 2.45(m, 4H), 2.76(q, 2H), 3.15(s, 3H), 5.48 (m, 1H), 7.09(d, 1H), 7.36(m, 2H), 7.70(d, 2H), 7.95(d, 2H), 8.46(d, 1H), 9.95(s, 1H) | 457 | Meth 61 |
| 11 | cyclobutyl | NH-CH₂-(tetrahydrofuran-2-yl) | 1.65(m, 10H), 2.50(s, 3H), 2.75(m, 2H), 3.65(m, 3H), 5.48(m, 1H), 7.07 (d, 1H), 7.46(s, 1H), 7.70(d, 2H), 7.94(d, 2H), 8.45(d, 1H), 9.95(s, 1H) | 469 | Meth 61 |
| 12[2,3] | cyclopentyl | NH-CH₂-(pyridin-2-yl) | 1.54(m, 2H), 1.72(m, 2H), 2.00(m, 2H), 2.19(m, 2H), 2.79(s, 3H), 4.38 (d, 2H), 5.54(quin, 1H), 7.25(d, 1H), 7.76(t, 3H), 7.89(d, 3H), 8.20 (s, 1H), 8.38(t, 1H), 8.60(brt, 1H), 8.72(d, 2H), 10.24(s, 1H) | 490 | Meth 62 |
| 13[2,3] | cyclopentyl | NH-CH₂CH₂CH₂-O-CH₂CH₃ | 1.53(m, 2H), 1.60(quin, 2H), 1.75 (m, 2H), 2.03(m, 2H), 2.18(m, 2H), 2.78(m, 5H), 3.17(s, 3H), 3.28(t, 2H), 5.55(quin, 1H), 7.26(d, 1H), 7.47(t, 1H), 7.72(d, 2H), 7.89(d, 2H), 8.20(s, 1H), 8.73(d, 1H), 10.20 (s, 1H) | 471 | Meth 62 |
| 14 | cyclobutyl | NH-C(CH₃)₃ | 1.08(s, 9H), 1.65(m, 2H), 2.37(m, 4H), 2.76(s, 3H), 5.42(m, 1H), 7.22 (d, 1H), 7.33(brs, 1H), 7.75(d, 2H), 7.92(d, 2H), 8.14(s, 1H), 8.68(d, 1H), 10.24(brs, 1H) | 441 | Meth 61 |
| 15 | cyclopropyl | NH-C(CH₃)₃ | 0.88(m, 2H), 1.07(m, 11H), 2.74(s, 3H), 3.79(m, 1H), 7.29(brs, 1H), 7.32(d, 1H), 7.74(d, 2H), 7.95(d, 2H), 8.18(s, 1H), 8.69(d, 1H), 10.22 (brs, 1H) | 427 | Meth 52 |
| 16 | cyclopropyl | NH-cyclopropyl | 0.33(m, 2H), 0.43(m, 2H), 0.88(m, 2H), 1.07(m, 2H), 2.09(m, 1H), 2.75 (s, 3H), 3.80(m, 1H), 7.33(d, 1H), 7.73(m, 3H), 8.0(d, 2H), 8.19(s, 1H), 8.7(d, 1H), 10.29(brs, 1H) | 416 | Meth 52 |
| 17 | cyclopropyl | NH-CH₂CH₂-O-CH₂-O-CH₃ | 0.70(m, 2H), 1.08(m, 5H), 2.48(s, 3H), 2.90(m, 2H), 3.33(m, 4H), 4.61 (m, 1H), 7.22(d, 1H), 7.45(s, 1H), 7.73(d, 2H), 8.01(d, 2H), 8.52(d, 1H), 9.99(s, 1H) | 443 | Meth 65 |
| 18 | cyclopropyl | NH-CH₂-CF₃ | 0.83(m, 2H), 1.05(m, 2H), 2.70(s, 3H), 3.56(m, 2H), 3.75(m, 1H), 7.29 (d, 1H), 7.71(d, 2H), 7.95(d, 2H), 8.13(s, 1H), 8.43(t, 1H), 8.65(d, 1H), 10.26(bs, 1H) | 453 | Meth 65 |

-continued

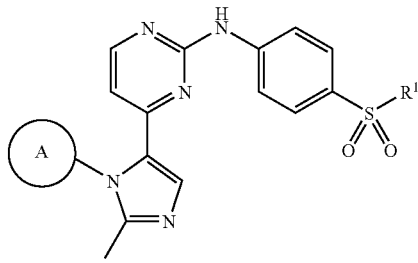

| Ex | Ring A | R¹ | NMR | M/z | SM |
|---|---|---|---|---|---|
| 19 | cyclobutyl | NH~~O~~ | 1.03(t, 3H), 1.68(m, 2H), 2.39(m, 4H), 2.76(s, 3H), 2.86(t, 2H), 3.32 (m, 4H), 5.42(m, 1H), 7.23(d, 1H), 7.56(bs, 1H), 7.74(d, 2H), 7.95(d, 2H), 8.14(s, 1H), 8.68(d, 1H), 10.29 (bs, 1H) | 457 | Meth 61 |

[1] Purified by Flash silica Chromatography DCM:MeOH (Polarity increasing from 100:0 to 98:2)
[2] 2 Equivalents of amine and then excess (~25 equivalents) of diethylmethylamine
[3] Purified by Isolute amine column

Examples 20-21

The following Examples were also prepared by the procedure of Example 1 using the appropriate starting materials.

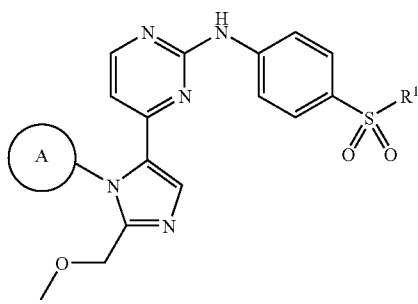

| Ex | Ring A | R¹ | NMR | M/z | SM |
|---|---|---|---|---|---|
| 20 | cyclobutyl | NH~~O~~ | 1.05(t, 3H), 1.68(m, 2H), 2.40(m, 4H), 2.83(m, 2H), 3.32(m, 4H), 3.45(s, 3H), 4.88(s, 2H), 5.43 (quintet, 1H), 7.29(d, 1H), 7.55(m, 1H), 7.75(d, 2H), 7.95(d, 2H), 8.24 (s, 1H), 8.70(d, 1H), 10.28(s, 1H) | 487 | Meth 63 |
| 21 | cyclopentyl | NH~~O~~ | 1.07(t, 3H), 1.49(m, 2H), 1.68(m, 2H), 2.00(m, 2H), 2.14(m, 2H), 2.88(m, 2H), 3.34(m, 4H), 3.47(s, 3H), 4.90(s, 2H), 5.48(quintet, 1H), 7.29(d, 1H), 7.58(s, 1H), 7.74(d, 2H), 7.89(d, 2H), 8.25(s, 1H), 8.72 (d, 1H), 10.20(s, 1H) | 501 | Meth 64 |

Example 22

4-(1-Methoxyprop-2-yl-2-methylimidazol-5-yl)-2-{4-[N-(tetrahydrofur-2-ylmethyl) sulphamoyl] anilino}pyrimidine To a stirred solution of 2-amino-4-(1-methoxyprop-2-yl-2-methylimidazol-5-yl)pyrimidine (Method 53; 118 mg, 0.75 mmol), N-(tetrahydrofur-2-ylmethyl)4-iodobenzenesulphonamide (Method 68; 413 mg, 1.13 mmol), tris(dibenzylideneacetone) dipalladium (0) (35 mg, 0.038 mmol) and 2,2'-bis(diphenylphosphino)-1,1'-binaphthyl (47 mg, 0.076 mmol) in dioxane (10 mL) was added sodium t-butoxide (258 mg, 2.69 mmol) and the mixture heated at 80° C. overnight. The reaction was cooled to room temperature and MeOH (5 ml) was added and the mixture poured onto an Isolute SCX-2 column, eluted first with MeOH (10×30 ml) and the product was then eluted with 10% methanolic ammonia (10×30 ml). The solvent was removed by evaporation and the residue purified by flash chromatography on silica gel eluting with DCM/MeOH (100:0 increasing in polarity to 97:3) to yield a foam which was dissolved in MeOH (2 ml) and treated with 1M HCl in ether (300 μL, 0.30 mmol) for 5 minutes. Solvent was evaporated in vacuo to yield a yellow solid (115 mg, 30%). NMR: 1.52 (d, 3H), 1.75 (m, 4H), 2.70 (m, 2H), 2.79 (s, 3H); 3.16 (s, 3H), 3.63 (m, 5H), 5.65 (m, 1H), 7.25 (d, 1H), 7.56 (t, 1H), 7.70 (d, 2H), 7.88 (d, 2H), 8.21 (s, 1H), 8.68 (d, 1H), 10.19 (brs, 1H); m/z 487.

Examples 23-39

The following Examples were prepared by the procedure of Example 22 using the appropriate starting materials.

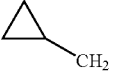

| Ex | R¹ | R² | NMR | M/z | SM |
|---|---|---|---|---|---|
| 23 | 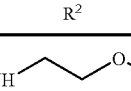 | 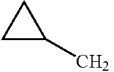 | 0.15(m, 2H), 0.35(m, 2H), 1.10 (m, 1H), 2.45(s, 3H), 2.95(q, 2H), 3.20(s, 3H), 3.30(q, 2H), 4.55(d, 2H), 7.20(d, 1H), 7.40 (t, 1H), 7.65(s, 1H), 7.70(d, 2H), 7.90(d, 2H), 8.45(d, 1H), 9.75(s, 1H) | 441 (M − H)⁻ | Meth 54 Meth 66 |
| 24 | 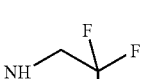 | 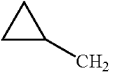 | 0.27(m, 2H), 0.40(m, 2H), 1.15 (m, 1H), 2.85(s, 3H), 3.65(m, 2H), 4.75(d, 2H), 7.40(d, 1H), 7.80(d, 2H), 7.90(d, 2H), 8.50 (s, 1H), 8.55(t, 1H), 8.70(d, 1H), 10.3(s, 1H) | 467 | Meth 54 Meth 71 |
| 25 | 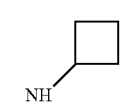 | 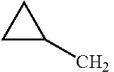 | 0.15(m, 2H), 0.33(m, 2H), 1.1 (m, 1H), 1.5(m, 2H), 1.75(m, 2H), 1.9(m, 2H), 2.45(s, 3H), 3.65(m, 1H), 4.6(d, 2H), 7.25 (d, 1H), 7.75(m, 4H), 7.9(d, 2H), 8.5(d, 1H), 9.9(s, 1H) | 439 | Meth 54 Meth 70 |
| 26 | 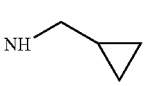 | 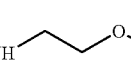 | 0.10(m, 2H), 0.25(m, 2H), 0.40 (m, 4H), 0.82(m, 1H), 1.15(m, 1H), 2.65(t, 2H), 2.75(s, 3H), 4.75(d, 2H), 7.40(d, 1H), 7.6(t, 1H), 7.8(d, 2H), 7.9(d, 2H), 8.50(s, 1H), 8.7(d, 1H), 10.25 (s, 1H) | 437 (M − H)⁻ | Meth 54 Meth 67 |
| 27 | cyclobutyl | 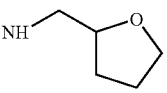 | 1.71(m, 2H), 2.34(m, 4H), 2.76 (s, 3H), 2.86(t, 2H), 3.16(s, 3H), 3.29(s, 2H), 5.41(m, 1H), 7.21(d, 1H), 7.52(brs, 1H), 7.76 (d, 2H), 7.93(d, 2H), 8.16(s, 1H), 8.68(d, 1H), 10.28(brs, 1H) | 443 | Meth 51 Meth 66 |
| 28 | 1-Methoxy-prop-2-yl | 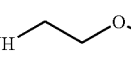 | 1.52(d, 3H), 2.76(s, 3H), 2.84 (q, 2H), 3.14(s, 3H), 3.16(s, 3H), 3.28(t, 2H), 3.36(m, 1H), 3.82(m, 1H), 5.65(m, 1H), 7.23 (d, 1H), 7.55(t, 1H), 7.74(d, 2H), 7.88(d, 2H), 8.21(s, 1H), 8.68(d, 1H), 10.19(brs, 1H) | 461 | Meth 53 Meth 68 |
| 29 | cyclopropyl | 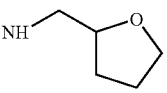 | 0.88(m, 2H), 1.13(m, 2H), 2.76 (2, 3H), 2.85(q, 2H), 3.16(s, 3H), 3.29(t, 2H), 3.75(m, 1H), 7.33(d, 1H), 7.50(t, 1H), 7.72 (d, 2H), 7.97(d, 2H), 8.16(s, 1H), 8.69(d, 1H), 10.26(brs, 1H) | 429 | Meth 52 Meth 66 |

-continued

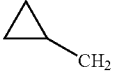

| Ex | R¹ | R² | NMR | M/z | SM |
|---|---|---|---|---|---|
| 30 | 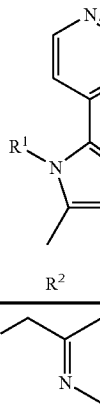 CH₂ |  | 0.28(m, 2H), 0.41(m, 2H), 1.18 (m, 1H), 2.78(s, 3H), 4.38(d, 2H), 4.78(d, 2H), 7.42(d, 1H), 7.77(t, 1H), 7.80(d, 2H), 7.88 (d, 1H), 7.93(d, 2H), 8.34(t, 1H), 8.50(s, 1H), 8.55(t, 1H), 8.72(d, 2H), 10.31(s, 1H) | 467 | Meth 54 Meth 69 |
| 31 | Tetrahydrofur-3-yl |  | 2.22(m, 1H), 2.58(m, 1H), 2.76 (s, 3H), 2.86(q, 2H), 3.16(s, 3H), 3.30(t, 2H), 3.54(m, 1H), 3.85(m, 1H), 4.18(m, 1H), 4.21 (m, 1H), 6.18(m, 1H), 7.27(d, 1H), 7.55(t, 1H), 7.71(d, 2H), 7.89(d, 2H), 8.20(s, 1H), 8.69 (d, 1H), 10.15(s, 1H) | 459 | Meth 55 Meth 66 |
| 32 | Tetrahydrofur-3-yl |  | 1.08(t, 3H), 2.29(m, 1H), 2.62 (m, 1H), 2.80(s, 3H), 2.89(m, 2H), 3.35(m, 4H), 3.59(m, 1H), 3.90(m, 1H), 4.20(m, 1H), 4.27 (m, 1H), 6.24(br m, 1H), 7.31 (d, 1H), 7.58(t, 1H), 7.75(d, 2H), 7.92(d, 2H), 8.30(s, 1H), 8.72(d, 1H), 10.24(s, 1H) | 473 | Meth 55 Meth 72 |
| 33 | Tetrahydrofur-3-yl | 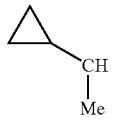 | 1.08(s, 9H), 2.27(m, 1H), 2.59 (m, 1H), 2.79(s, 3H), 3.54(q, 1H), 3.84(t, 1H), 4.19(t, 1H), 4.24(d, 1H), 6.19(br m, 1H) 7.28(d, 1H), 7.36(s, 1H), 7.74 (d, 2H), 7.88(d, 2H), 8.27(s, 1H), 8.70(d, 1H), 10.20(s, 1H) | 457 | Meth 55 Meth 73 |
| 34 |  CH Me |  | 0.11(m, 1H), 0.40(m, 2H), 0.60 (m, 1H), 1.45(m, 1H), 1.62(d, 3H), 2.85(s, 3H), 2.88(m, 2H), 3.19(s, 3H), 3.32(t, 3H), 4.77 (m, 1H), 7.27(d, 1H), 7.58(t, 1H), 7.73(d, 2H), 7.85(d, 2H), 8.25(s, 1H), 8.70(d, 1H), 10.03 (s, 1H). | 457 | Meth 57 Meth 66 |
| 35 | 1-Methoxy-prop-2-yl | 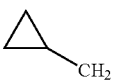 | 1.03(t, 3H), 1.52(d, 3H), 2.80 (s, 3H), 2.87(m, 2H), 3.16(s, 3H), 3.30(m, 4H), 3.58(m, 1H), 3.85(t, 1H), 5.68(m, 1H), 7.25 (d, 1H), 7.50(m, 1H), 7.72(d, 2H), 7.85(d, 2H), 8.21(s, 1H), 8.70(d, 1H), 10.19(s, 1H) | 475 | Meth 53 Meth 72 |
| 36 |  CH₂ | 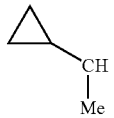 | 0.13(m, 2H), 0.10(m, 2H), 1.00 (m, 4H), 2.35(s, 3H), 2.85(q, 2H), 3.30(m, 4H), 4.55(d, 2H), 7.21(d, 1H), 7.45(t, 1H), 7.63 (s, 1H), 7.67(d, 2H), 7.85(d, 2H), 8.45(d, 1H), 9.85(s, 1H) | 457 | Meth 54 Meth 72 |
| 37 |  CH Me |  | 0.10(m, 1H), 0.48(m, 2H), 0.60 (m, 1H), 1.05(t, 3H), 1.44(m, 1H), 1.61(d, 3H), 2.48(m, 5H), 3.33(m, 4H), 4.74(m, 1H), 7.24 (d, 1H), 7.53(t, 1H), 7.71(d, 2H), 7.84(d, 2H), 8.22(s, 1H), 8.68(d, 1H), 10.11(s, 1H) | 471 | Meth 57 Meth 72 |

-continued

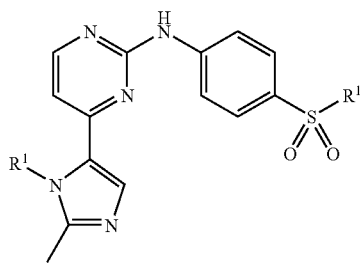

| Ex | R¹ | R² | NMR | M/z | SM |
|----|----|----|-----|-----|-----|
| 38 | cyclopropyl-CH(Me)- | NH-cyclopropyl | 0.10(m, 1H), 0.38(m, 4H), 0.45 (m, 2H), 0.59(m, 1H)1.44(m, 1H), 1.63(d, 3H), 2.10(m, 1H), 2.84(s, 3H), 4.76(m, 1H), 7.26 (d, 1H), 7.72(d, 3H), 7.87(d, 2H), 8.23(s, 1H), 8.69(d, 1H), 10.12(s, 1H) | 439 | Meth 57 Meth 74 |
| 39 | cyclopropyl-CH(Me)- | NH-CH₂-(tetrahydrofuran-2-yl) | 0.10(m, 1H), 0.38(m, 2H), 0.60 (m, 1H), 1.50(m, 2H), 1.63(d, 3H), 1.77(m, 3H), 2.75(m, 2H), 2.83(s, 3H), 3.56(m, 1H), 3.68 (m, 1H), 3.79(m, 1H), 4.27(m, 1H), 7.50(d, 1H), 7.56(t, 1H), 7.71(d, 2H), 7.82(d, 2H), 8.23 (s, 1H), 8.68(d, 1H), 10.10(s, 1H) | 483 | Meth 57 Meth 68 |

Examples 40-47

The following Examples were also prepared by the procedure of Example 22 using the appropriate starting materials.

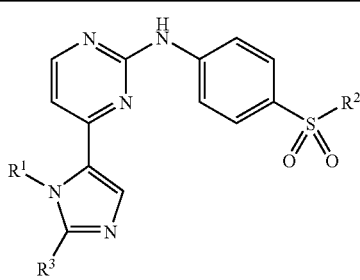

| Ex | R¹ | R² | R³ | NMR | M/z | SM |
|----|----|----|-----|-----|-----|-----|
| 40 | cyclopropyl-CH(Me)- | NH-CH₂CH₂-OMe | CH₂OMe | 0.13(m, 1H), 0.38(m, 2H), 0.61(m, 1H), 1.43 (m, 1H), 1.65(d, 3H), 2.90(q, 2H), 3.19(s, 3H) 3.32(t, 2H), 3.44(s, 3H), 4.69(m, 1H), 4.93(q, 2H), 7.30(d, 1H), 7.58 (t, 1H), 7.73(d, 2H), 7.86(d, 2H), 8.23(s, 1H), 8.69(d, 1H), 10.13 (s, 1H). | 487 | Meth 58 Meth 66 |

-continued

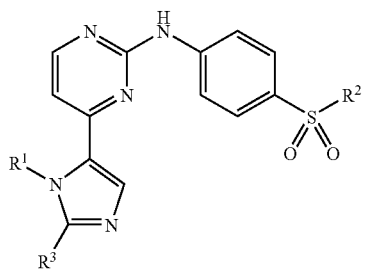

| Ex | R¹ | R² | R³ | NMR | M/z | SM |
|---|---|---|---|---|---|---|
| 41 | cyclopropyl-CH(Me)- | NH-CH₂CH₂-O-CH₂- | CH₂OMe | 0.13(m, 1H), 0.38(m, 2H), 0.61(m, 1H), 1.05 (t, 3H), 1.42(m, 1H), 1.64(d, 3H), 2.88(q, 2H), 3.36(m, 4H), 3.45 (s, 3H), 4.68(m, 1H), 4.93(q, 2H), 7.30(d, 1H), 7.58(t, 1H), 7.73 (d,.2H), 7.86(d, 2H), 8.23(s, 1H), 8.69(d, 1H), 10.13(s, 1H). | 501 | Meth 58 Meth 72 |
| 42 | 1-Methoxy-prop-2-yl | NH-CH₂CH₂-O-Et | Et | 1.04(t, 3H), 1.35(t, 3H), 1.52(d, 3H), 2.85(q, 2H), 3.15(m, 5H), 3.34 (m, 4H), 3.59(m, 1H), 3.83(t, 1H), 5.57(s, 1H), 7.27(d, 1H), 7.54(t, 1H), 7.73(d, 2H), 7.89 (d, 2H), 8.23(s, 1H), 8.70(d, 1H), 10.19(s, 1H) | 489 | Meth 59 Meth 72 |
| 43 | 1-Methoxy-prop-2-yl | NH-CH₂-(tetrahydrofuran-2-yl) | Et | 1.35(t, 3H), 1.52(q, 4H), 1.75(m, 2H), 1.86 (m, 1H) 2.74(m, 2H), 3.13(m, 5H), 3.57(m, 2H), 3.68(m, 1H), 3.80 (m, 2H), 5.57(s, 1H), 7.26(d, 1H), 7.57(t, 1H), 7.73(d, 2H), 7.88 (d, 2H), 8.23(s, 1H), 8.70(d, 1H), 10.16(s, 1H) | 501 | Meth 59 Meth 68 |
| 44 | 1-Methoxy-prop-2-yl | NH-CH₂CH₂-OMe | Et | 1.35(t, 3H), 1.53(d, 3H), 2.89(m, 2H), 3.16 (m, 8H), 3.29(m, 2H), 3.55(m, 1H), 3.80(m, 1H), 5.58(s, 1H), 7.25 (d, 1H), 7.57(t, 1H), 7.73(d, 2H), 7.89(d, 2H), 8.24(s, 1H), 8.70 (d, 1H), 10.19(s, 1H) | 475 | Meth 59 Meth 66 |
| 45 | 1-Methoxy-prop-2-yl | NH-cyclopropyl | Et | 0.35(m, 2H), 0.48(m, 2H), 1.37(t, 3H), 1.54 (d, 3H), 2.10(m, 1H), 3.14(m, 5H), 3.59(m, 1H), 3.88(m, 1H). 5.60 (s, 1H), 7.27(d, 1H), 7.75(m, 3H), 7.91(d, 2H), 8.24(s, 1H), 8.73 (d, 1H), 10.21(s, 1H) | 457 | Meth 59 Meth 74 |

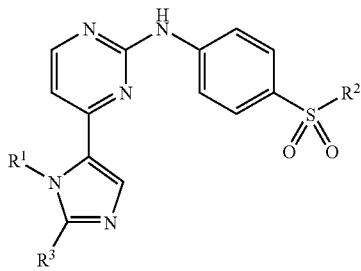

| Ex | R¹ | R² | R³ | NMR | M/z | SM |
|---|---|---|---|---|---|---|
| 46 | 1-Methoxy-prop-2-yl | NH~~~O~ | n-Pr | 1.0(t, 3H), 1.5(d, 3H), 1.8(sext, 2H), 2.87(q, 2H), 3.05(t, 2H), 3.11(s, 3H), 3.16(s, 3H), 3.28(t, 2H), 3.56(q, 1H), 3.80 (t, 1H), 5.52(s, 1H), 7.23 (d, 1H), 7.55(t, 1H) 7.71(d, 2H), 7.85(d, 2H), 8.16(s, 1H), 8.68 (d, 1H), 10.12(s, 1H) | 489 | Meth 60 Meth 66 |
| 47 | 1-Methoxy-prop-2-yl | NH~~~O~~~ | n-Pr | 1(t, 3H), 1.03(t, 3H), 1.51(d, 3H), 1.8(sext, 2H), 2.85(q, 2H), 3.05 (t, 2H), 3.32(t + q, 4H), 3.56(q, 1H), 3.8(t, 1H), 5.51(s, 1H), 7.23(d, 1H), 7.51(t, 1H), 7.71 (d, 2H), 7.87(d, 2H), 8.13(s, 1H), 8.67(d, 1H), 10.11(s, 1H) | 503 | Meth 60 Meth 72 |

Example 48

4-(1-Cyclopropylmethyl-2-ethylimidazol-5-yl)-2-{4-[N-(2-methoxyethyl) sulphamoyl] anilino}pyrimidine Anisole (4.57 ml) followed by trifluoroacetic acid (22 ml) was added to 4-(1-cyclopropylmethyl-2-ethylimidazol-5-yl)-2-{4-[N-(2-methoxyethyl)-N-(t-butyl)sulphamoyl] anilino}pyrimidine (Method 76; 3.7 g, 7.22 mmol). The mixture was stirred at ambient temperature for two hours, the volatiles were evaporated and the residue dissolved in water and then extracted with EtOAc. The aqueous layer was neutralised with saturated aqueous sodium hydrogen carbonate solution and extracted with EtOAc. The extract was dried and the solvent removed by evaporation. The residue was purified by chromatography on silica gel eluting with EtOAc/MeOH (100:0 increasing in polarity to 98:2) to give the title compound (1.58 g, 48%) as a foam. NMR: 0.00-0.02 m, 2H), 0.18-0.20 m, 2H), 0.86-0.90 (m, 1H), 1.10 (t, 3H), 2.60 (q, 2H), 2.75 (q, 2Hy, 3.01 (s, 3H>, 3.18 (q, 2H), 4.40 (d, 2H), 7.10 (d, 1H), 7.35 (t, 1H), 7.52 (s, 1H), 7.57 (d, 2H), 7.77 (d, 2H), 8.30 (d, 1H), 9.70 (s, 1H); m/z 457.

Example 49

4-(1-Benzyl-2-methylimidazol-5-yl)-2-[4-(N-methylsulphamoyl)anilino]pyrimidine 4-Amino-N-methyl-benzenesulphonamide (250 mg, 1.34 mmol) was dissolved in the minimum amount of MeOH and 1M ethereal hydrogen chloride (1.34 ml) added. The volatiles were removed by evaporation and cyanamide (68 mg, 1.62 mmol) was added followed by dimethylacetamide (0.5 ml) and the mixture heated at 100° C. for 45 minutes. The mixture was allowed to cool and 1-benzyl-5-(3-dimethylaminoprop-2-en-1-oyl)-2-methylimidazole (Method 50; 230 mg, 0.86 mmol) and sodium methoxide (150 mg, 2.78 mmol) were added and the mixture heated to reflux for one hour. The mixture allowed to cool and was partitioned between EtOAc and aqueous sodium hydrogen carbonate solution. The organic layer was separated, washed with brine, dried (Na₂SO₄) and the volatiles removed by evaporation. The residue was purified by chromatography on silica eluting with DCM/7N methanolic ammonia (96:4). The purified product was triturated with minimal hot EtOAc to give the title compound (260 mg, 70%) as a cream solid. NMR: 2.28 (s, 3H), 2.37 (d, 3H), 5.96 (s, 2H), 6.93 (d, 2H), 7.15-7.28 (m, 5H), 7.54 (d, 2H), 7.75-7.81 (m, 3H), 8.40 (d, 1H), 9.86 (s, 1H); m/z 435.

Example 50

4-(1-Cyclopropylmethyl-2-(2-methylprop-1-enyl) imidazol-5-yl)-2-{4-[N-(2-methoxyethyl) sulphamoyl]anilino}pydrimidine Anisole (146 µl, 1.34 mmol) followed by 90% trifluoroacetic acid in water (10 ml) was added to 4-(1-cyclopropylmethyl-2-(2-methylprop-1-enyl)imidazol-5-yl)-2-{4-[N-(2-methoxyethyl)-N-(t-butyl)sulphamoyl]anilino}pyrimidine (Method 80; 120 mg, 0.22 mmol) and the mixture was stirred at ambient temperature for one hour. The solution was extracted with ether and remaining aqueous layer was neutralised to pH 7 then extracted with EtOAc. The EtOAc extracts were combined, dried and the volatiles removed by evaporation to give title compound (30 mg, 41%) as a solid. NMR: 0.15 (q, 2H), 0.32 (q, 2H), 1.01 (t, 1H), 1.99(s, 3H), 2.18 (s, 3H), 2.87 (q, 2H), 3.18 (s, 3H), 4.65 (d, 2H), 6.30 (s, 1H), 7.29 (d, 1H), 7.50 (t, 1H), 7.71 (d, 2H), 7.82 (s, 1H), 7.90 (d, 2H), 8.47 (d, 1H), 9.87 (s, 1H); m/z 457.

Preparation of Starting Materials

The starting materials for the examples above are either commercially available or are readily prepared by standard methods from known materials. For example, the following reactions are an illustration, but not a limitation, of some of the starting materials used in the above reactions.

Methods 1-36

The following compounds were prepared using procedures analogous to those described in JOC 1987, 2714-2726.

| Meth | Compound | NMR | m/z | SM |
|---|---|---|---|---|
| 1 | 5-Methyl-4-(N-cyclobutylamino)isoxazole | 1.63(m, 4H), 2.21(m, 5H), 3.56(s, 2H), 4.42(m, 1H), 8.14(s, 1H) | 153 | 5-Methyl-4-aminoisoxazole hydrochloride |
| 2 | 5-Methyl-4-(N-cyclobutyl-N-acetamido)isoxazole | 1.60(m, 7H), 2.01(m, 2H), 2.32(s, 3H), 4.91(m, 1H), 8.62(s, 1H) | 195 | Meth 1 |
| 3 | 1-cyclobutyl-2-methyl-5-acetylimidazole | 1.72(m, 2H), 2.28(m, 2H), 2.38(s, 3H), 2.48(s, 3H), 2.58(m, 2H), 5.20(m, 1H), 7.79(s, 1H) | | Meth 2 |
| 4 | 5-Methyl-4-(N-methoxyisopropyl amino)isoxazole | 1.01(d, 3H), 2.06(s, 3H), 3.05(m, 2H), 3.19(m, 6H), 2.92(m, 1H), 8.26(s, 1H) | 171 | 5-Methyl-4-aminoisoxazole hydrochloride |
| 5 | 5-Methyl-4-(N-methoxyisopropyl-N-acetamido)isoxazole | 0.90(d, 3H), 1.70(s, 3H), 2.36(s, 3H), 3.05(m, 2H), 3.19(s, 3H), 4.82(m, 1H), 8.50(m, 1H) | | Meth 4 |
| 6 | 1-methoxyisopropyl-2-methyl-5-acetylimidazole | 1.36(d, 3H), 2.36(s, 3H), 2.38(s, 3H), 3.14(s, 3H), 3.52(dd, 1H), 3.82(m, 1H), 4.96(m, 1H), 7.85(s, 1H) | 197 | Meth 5 |
| 7 | 5-Methyl-4-(N-cyclopropyl carboxamido)isoxazole | 0.90(m, 2H), 1.05(m, 2H), 1.50(m, 1H), 1.98(s, 3H), 7.20(brs, 1H), 8.50(s, 1H) | 165 [M − H]⁻ | 5-Methyl-4-aminoisoxazole hydrochloride |
| 8 | 5-Methyl-4-(N-cyclopropylmethyl amino)isoxazole | 0.10(m, 2H), 0.53(m, 2H), 1.00(m, 1H), 2.30(s, 3H), 2.82(d, 2H), 8.02(s, 1H) | 153 | Meth 7 |
| 9 | 5-Methyl-4-(N-cyclopropylmethyl-N-acetamido)isoxazole | 0.15(m, 2H), 0.48(m, 2H), 0.90(m, 1H), 1.90(s, 3H), 2.40(s, 3H), 3.45(d, 2H), 8.20(s, 1H) | 195 | Meth 8 |
| 10 | 1-cyclopropylmethyl-2-methyl-5-acetylimidazole | 0.35(m, 2H), 0.50(m, 2H), 1.10-1.30(br m, 2H), 2.45(s, 6H), 4.21(d, 2H), 7.75(s, 1H) | 179 | Meth 9 |
| 11 | 5-Methyl-4-(N-cyclopropylamino)isoxazole | 0.26(m, 2H), 0.46(m, 2H), 2.16(s, 3H), 2.22(m, 1H), 4.81(m, 1H), 8.16(s, 1H) | 139 | 5-Methyl-4-aminoisoxazole hydrochloride |
| 12 | 5-Methyl-4-(N-cyclopropyl-N-acetamido)isoxazole | Used Crude | 181 | Meth 11 |
| 13 | 1-cyclopropyl-2-methyl-5-acetylimidazole | Used Crude | 165 | Meth 12 |
| 14 | 5-Methyl-4-(N-cyclopentylamino)isoxazole | Used Crude | 167 | 5-Methyl-4-aminoisoxazole hydrochloride |
| 15 | 5-Methyl-4-(N-cyclopentyl-N-acetamido)isoxazole | 1.13(m, 2H), 1.45(m, 2H), 1.71(m, 4H), 2.31(s, 3H), 3.27(s, 3H), 4.73(m, 1H), 8.61(s, 1H) | 209 | Meth 14 |
| 16 | 1-cyclopentyl-2-methyl-5-acetylimidazole | (CDCl₃) 1.68(m, 2H), 2.00(m, 6H), 2.43(s, 3H), 2.51(s, 3H), 5.21(quin, 1H), 7.73(s, 1H) | 193 | Meth 15 |
| 17 | 5-Methyl-4-[N-(tetrahydrofur-3-yl)amino]isoxazole | (CDCl₃) 1.80(m, 1H), 2.15(m, 1H), 2.31(s, 3H), 2.59(brs, 1H), 3.66(q, 1H), 3.79(m, 3H), 3.98(m, 1H), 8.02(s, 1H) | 169 | 5-Methyl-4-aminoisoxazole hydrochloride |
| 18 | 5-Methyl-4-[N-(tetrahydrofur-3-yl)-N-acetamido]isoxazole | (CDCl₃) 1.58(brs, 1H), 1.82(s, 3H), 2.18(m, 1H), 2.29(s, 3H), 3.64(m, 3H), 3.85(m, 1H), 5.16(brs, 1H), 8.11(s, 1H) | 211 | Meth 17 |

-continued

| Meth | Compound | NMR | m/z | SM |
|---|---|---|---|---|
| 19 | 1-(tetrahydrofur-3-yl)-2-methyl-5-acetylimidazole | (CDCl$_3$) 2.18(m, 2H), 2.46(s, 3H), 2.59(s, 3H), 3.81(q, 1H), 4.00(m, 2H), 4.32(m, 1H), 6.05(m, 1H), 7.72(s, 1H) | 213 | Meth 18 |
| 20 | 5-Methyl-4-(N-cyclopropylmethyl-N-propionamido)isoxazole | 0.02(d, 2H), 0.39(d, 2H), 0.83-0.78(m, 1H), 0.92(t, 3H), 1.99(q, 2H), 2.38(s, 3H), 3.33(d, 2H), 8.62(s, 1H) | | Meth 8 |
| 21 | 1-Cyclopropylmethyl-2-ethyl-5-acetylimidazole | 0.03-0.01(m, 2H), 0.19-0.16(m, 2H), 2.10(s, 3H), 2.41(q, 2H), 3.89(d, 2H), 7.60(s, 1H) | 193 | Meth 20 |
| 22 | 5-Methyl-4-[N-(1-cyclopropylethyl)amino]isoxazole | 0.14(m, 2H), 0.36(m, 2H), 0.78(m, 1H), 1.10(d, 3H), 2.28(s, 3H), 2.47(m, 1H), 3.94(d, 1H), 8.23(s, 1H). | 167 | 5-Methyl-4-aminoisoxazole hydrochloride |
| 23 | 5-Methyl-4-[N-(1-cyclopropylethyl)-N-acetamido]isoxazole | 0.27(br s, 2H), 0.47(br s, 3H), 1.05(br s, 3H), 1.72(s, 3H), 2.39(s, 3H), 3.92(m, 1H), 8.61(s, 1H) | 209 | Meth 22 |
| 24 | 1-(1-Cyclopropylethyl)-2-methyl-5-acetylimidazole | [400MHz, 373°K] 0.12(m, 1H), 0.39(m, 2H), 0.64(m, 1H), 1.52(d, 3H), 1.59(m, 1H), 2.42(s, 3H), 2.58(s, 3H), 4.32(m, 1H), 7.78(s, 1H) | 193 | Meth 23 |
| 25 | 5-Methyl-4-[N-(1-cyclopropylethyl)-N-methoxyacetamido]isoxazole | 0.30(s, 2H), 0.50(m, 3H), 1.09(m, 3H), 2.39(s, 3H), 3.20(s, 3H), 3.67(m, 2H), 3.91(m, 1H), 8.61(s, 1H) | 237 (M − H)⁻ | Meth 22 |
| 26 | 1-(1-Cyclopropylethyl)-2-(methoxymethyl)-5-acetylimidazole | 0.17(m, 1H), 0.30(m, 2H). 0.59(m, 1H), 1.52(d, 3H), 1.71(m, 1H), 2.44(s, 3H), 3.244(s, 3H), 4.50(m, 2H), 7.96(s, 1H) | 223 | Meth 25 |
| 27 | 5-Methyl-4-[N-cyclobutyl amino]isoxazole | (CDCl$_3$) 1.76(m, 4H), 2.31(m, 4H), 2.56(m, 1H), 3.62(m, 1H), 7.96(s, 1H) | 153 | 5-Methyl-4-aminoisoxazole hydrochloride |
| 28 | 5-Methyl-4-[N-cyclobutyl-N-methoxyacetamido]isoxazole | 1.36(m, 2H), 1.48(m, 2H), 1.64(m, 2H), 1.76(m, 2H), 2.25(s, 3H), 3.45(m, 1H), 4.05(br d, 1H), 8.23(s, 1H) | 167 | Meth 27 |
| 29 | 1-Cyclobutyl-2-methoxymethyl-5-acetylimidazole | 1.87(m, 2H), 2.40(m, 2H), 2.50(s, 3H), 2.71(m, 2H), 3.36(s, 3H), 4.60(s, 2H), 5.28(quin, 1H), 7.74(s, 1H) | NA | Meth 28 |
| 30 | 5-Methyl-4-[N-cyclopentyl amino]isoxazole | (CDCl$_3$) 1.5-1.8(m, 4H), 2.12(m, 2H), 2.34(s, 3H), 3.33(s, 3H), 3.68(s, 2H), 5.10(m, 1H), 8.10(s, 1H) | 225 | 5-Methyl-4-aminoisoxazole hydrochloride |
| 31 | 5-Methyl-4-[N-cyclopentyl-N-methoxyacetamido]isoxazole | 1.0-1.3(br m, 2H), 1.46(m, 4H), 1.77(m, 2H), 2.32(s, 3H), 3.18(s, 3H), 3.62(s, 2H), 4.75(m, 1H), 8.63(s, 1H) | 239 | Meth 30 |
| 32 | 1-Cyclopentyl-2-methoxymethyl-5-acetylimidazole | 1.68(m, 2H), 2.05(m, 6H), 2.49(s, 3H), 3.36(s, 3H), 4.60(s, 2H), 5.09(m, 1H), 7.79(s, 1H) | 223 | Meth 31 |
| 33 | 5-Methyl-4-(N-methoxyisopropyl-N-propionamido)isoxazole | 0.90(m, 6H). 1.85(q, 2H), 2.32(s, 3H), 3.10(m, 5H), 4.85(m, 1H), 8.50(m, 1H) | 227 | Meth 4 |
| 34 | 1-Methoxyisopropyl-2-ethyl-5-acetylimidazole | 1.20(t, 3H), 1.35(d, 3H), 2.40(s, 3H), 2.70(q, 2H), 3.15(s, 3H), 3.55(m, 1H), 3.82(m, 1H), 4.85(m, 1H), 7.91(s, 1H) | 211 | Meth 33 |
| 35 | 5-Methyl-4-(N-methoxyisopropyl-N-butrylamido)isoxazole | 0.86(t, 3H), 1.0(d, 3H), 1.60(sext, 2H), 1.96(t, 2H), 2.38(s, 3H), 3.16(d, 2H), 3.28(s, 3H), 8.12(s, 1H) | NA | Meth 4 |
| 36 | 1-Methoxyisopropyl-2-propyl-5-acetylimidazole | 0.94(t, 3H), 1.38(d, 3H), 1.7(sext, 2H), 2.40(s, 3H), 2.68(t, 2H), 3.14(s, 3H), 3.56(q, 1H), 3.82(t, 1H), 4.84(s, 1H), 7.9(s, 1H) | 225 | Meth 35 |

Method 37

5-(3-Dimethylaminoprop-2-enoyl)-1-cyclobutyl-2-methylimidazole

1-Cyclobutyl-2-methyl-4-acetylimidazole (Method 3; 2.52 g, 14.1 mmol) was dissolved in DMF.DMA (75 mL) and the mixture heated at reflux, under an atmosphere of nitrogen, for 54 hours. The reaction mixture was allowed to cool to ambient temperature the product crystallised. The solid product was collected by filtration, washed with DMF.DMA and then ether and dried under vacuum at 40° C. to give the title compound (1.55 g, 47%) as a pale brown crystalline solid. NMR: 1.72 (m, 2H), 2.28 (m, 2H), 2.39 (s, 3H), 2.64 (m, 2H), 2.95 (m, 6H), 5.22 (m, 1H), 5.50 (d, 1H), 7.39 (s, 1H), 7.51 (d, 1H).

Methods 38-50

The following compounds were prepared by the procedure of Method 37 using the appopriate starting materials.

| Meth | Compound | NMR | m/z | SM |
|---|---|---|---|---|
| 38 | 5-(3-Dimethylaminoprop-2-en-1-oyl)-1-cyclopropyl-2-methylimidazole | 0.65(m, 2H), 1.00(m. 2H), 2.36(s, 3H), 2.95(m, 6H), 3.26(m, 1H), 5.42(d, 1H), 7.30(s, 1H), 7.50(d, 1H) | | Meth 13 |
| 39 | 5-(3-Dimethylaminoprop-2-en-1-oyl)-1-methoxy isopropyl-2-methylimidazole | 1.39(d, 3H), 2.36(s, 3H), 2.95(m, 6H), 3.15(s, 3H), 3.55(m, 1H), 3.87(m, 1H), 5.12(m, 1H), 5.55(d, 1H), 7.45(m, 2H) | 252 | Meth 6 |
| 40 | 5-(3-Dimethylaminoprop-2-en-1-oyl)-1-cyclopentyl-2-methylimidazole | (CDCl$_3$) 1.67(m, 2H), 2.03(m, 6H), 2.49(s, 3H), 3.00(m, 6H), 5.35(quin, 1H), 5.51(d, 1H), 7.48(s, 1H), 7.61(d, 1H) | 248 | Meth 16 |
| 41 | 5-(3-Dimethylaminoprop-2-en-1-oyl)-1-cyclopropylmethyl-2-methylimidazole | 0.35(m, 2H), 0.48(m, 2H), 1.20(m, 1H), 2.42(s, 3H), 3.00(brs, 6H), 4.30(d, 2H), 5.55(d, 1H), 7.50(s, 1H), 7.65(d, 1H) | 234 | Meth 10 |
| 42 | 5-(3-Dimethylaminoprop-2-en-1-oyl)-1-(tetrahydrofur-3-yl)-2-methylimidazole | (CDCl$_3$) 2.22(m, 1H), 2.48(m, 1H), 2.55(s, 3H), 3.00(brs, 6H), 3.79(q, 1H), 4.00(m, 1H), 4.07(m, 1H), 4.30(m, 1H), 5.52(d, 1H), 6.14(m, 1H), 7.48(s, 1H), 7.53(d, 1H) | 250 | Meth 19 |
| 43 | 5-(3-Dimethylaminoprop-2-en-1-oyl)-1-cyclopropylmethyl-2-ethylimidazole | 0.03-0.01(m, 2H), 0.18-0.09(m, 2H), 0.89-0.82(m, 1H), 0.98(t, 3H), 2.40(q, 2H), 2.72(s, 6H), 4.0(d, 2H), 5.35(d, 1H), 7.24(d, 1H), 7.50(s, 1H) | No m/s | Meth 21 |
| 44 | 5-(3-Dimethylaminoprop-2-en-1-oyl)-1-(1-cyclopropylethyl)-2-methylimidazole | [400MHz, 373°K] 0.15(m, 1H), 0.35(m, 2H), 0.63(m, 1H), 1.53(d, 3H), 1.62(m, 1H), 2.45(s, 3H), 2.96(m, 6H), 4.49(quin, 1H), 5.53(d, 1H), 7.43(s, 1H), 7.51(d, 1H) | 248 | Meth 24 |
| 45 | 5-(3-Dimethylaminoprop-2-en-1-oyl)-1-(1-cyclopropylethyl)-2-(methoxymethyl)imidazole | 0.16(m, 1H), 0.26(m, 2H), 0.57(m, 1H), 1.58(d, 3H), 1.77(m, 1H), 2.97(m, 6H), 3.24(s, 3H), 4.02(br s, 1H), 4.45(q, 2H), 5.61(d, 1H), 7.55(d, 1H), 7.62(s, 1H) | 278 | Meth 26 |
| 46 | 5-(3-Dimethylaminoprop-2-en-1-oyl)-1-cyclobutyl-2-methoxymethylimidazole | 1.71(m, 2H), 2.27(m, 2H), 2.68(m, 2H), 2.88(br s, 3H), 3.07(br s, 3H), 3.28(s, 3H), 4.48(s, 2H), 5.19(quintet, 1H), 5.54(d, 1H), 7.45(s, 1H), 7.58(d, 1H) | 263 | Meth 29 |
| 47 | 5-(3-Dimethylaminoprop-2-en-1-oyl)-1-cyclopentyl-2-methoxymethylimidazole | 1.56(m, 2H), 1.87(m, 4H), 2.14(m, 2H), 2.96(m, 6H), 3.23(s, 3H), 4.48(s, 2H), 5.00(m, 1H), 5.58(d, 1H) 7.55(m, 2H) | 278 | Meth 32 |
| 48 | 5-(3-Dimethylaminoprop-2-en-1-oyl)-1-methoxy isopropyl-2-ethylimidazole | 1.20(t, 3H), 1.40(d, 3H), 2.70(q, 2H), 2.95(br s, 6H), 3.15(s, 3H), 3.60(m, 1H), 3.86(m, 1H), 4.92(s, 1H), 5.55(d, 1H), 7.50(m, 2H) | 266 | Meth 34 |
| 49 | 5-(3-Dimethylaminoprop-2-en-1-oyl)-1-methoxy isopropyl-2-propylimidazole | 0.93(t, 3H), 1.40(d, 3H), 1.69(sext, 2H), 2.64(t, 2H), 2.94(m, 6H), 3.14(s, 3H), 3.6(q, 1H), 3.91(t, 1H), 4.91(s, 1H), 5.57(d, 1H), 7.51(d, 1H), 7.54(s, 1H) | 280 | Meth 36 |
| 50[1] | 1-Benzyl-5-(3-dimethylaminoprop-2-en-1-oyl)-2-methylimidazole | 2.21(s, 3H), 2.8-3.1(br s, 6H), 5.61(d, 1H), 5.68(s, 2H), 6.95-7.00(m, 2H), 7.15-7.3(m, 3H), 7.50(d, 1H), 7.65(s, 1H) | 270 | Meth 77 |

[1]Mixture heated at reflux for 3 hours and purified by chromatography on silica eluting with DCM/7M methanolic ammonia(98:2).

Method 51

2-Amino-4-(1-cyclobutyl-2-methylimidazol-5-yl)pyrimidine 5-(3-Dimethylaminoprop-2-en-1-oyl)-1-cyclobutyl-2-methylimidazole (Method 37; 466 mg, 2 mmol) and guanidine hydrochloride (476 mg, 5 mmol) were suspended in 1-butanol (10 ml). Sodium methoxide (432 g, 8 mmol) was added in one portion and the mixture heated under reflux, under an atmosphere of nitrogen, for 2 hours. The reaction mixture was allowed to cool to ambient temperature and was pre-absorbed on to silica gel and purified by column chromatography on silica gel eluting with DCM/2% methanolic ammonia (100:0 increasing in polarity to 97:3) to give the title compound (301 g, 66%). NMR: 1.73 (m, 2H), 2.45 (m, 7H), 5.36 (m, 1H), 6.58 (s, 2H), 6.72 (d, 1H), 7.24 (s, 1H), 8.16 (d, 1H); m/z 230

Methods 52-60

The following compounds were prepared by the procedure of Method 51 using the appropriate starting materials.

Method 61

2-Anilino-4-(1-cyclobutyl-2-methylimidazol-5-yl)pyrimidine 5-(3-Dimethylaminoprop-2-en-1-oyl)-1-cyclobutyl-2-methylimidazole (Method 37; 466 mg, 2 mmol), phenylguanidine hydrogen carbonate (434 g, 2.2 mmol) and sodium methoxide (238 mg, 4.4 mmol) were suspended in anhydrous DMA (5 ml) and the mixture heated at 160° C. for 3 hours. The reaction mixture was allowed to cool to ambient temperature and poured into water (50 ml). The solution was extracted EtOAc (2×50 ml). The combined extracts were washed with water (2×50 ml) and then brine (2×50 ml), dried and the volatiles removed by evaporation. The residue was triturated with ether, collected by filtration and air dried to give the title compound (205 mg, 35%) as a brown solid. NMR: 1.63 (m, 2H), 2.35 (m, 4H), 2.53 (s, 3H), 5.5 (m, 1H), 6.96 (d, 2H), 7.28 (m, 4H), 7.70 (d, 2H), 8.39 (d, 1H), 9/45 (s, 1H); m/z 306.

| Meth | Compound | NMR | m/z | SM |
|---|---|---|---|---|
| 52 | 2-Amino-4-(1-cyclopropyl-2-methylimidazol-5-yl)pyrimidine | 0.65(m, 2H), 1.08(m. 2H), 2.39(s, 3H), 3.42(m, 1H), 6.43(s, 2H), 6.82(d, 1H), 7.24(s, 1H), 8.18(d, 1H) | 216 | Meth 38 |
| 53 | 2-Amino-4-(1-methoxyisopropyl-2-methylimidazol-5-yl)pyrimidine | 1.43(d, 3H), 2.40(s, 3H), 3.15(s, 3H), 3.58(m, 1H), 3.91(m, 1H), 5.36(m, 1H), 6.49(s, 2H), 6.74(d, 1H), 7.33(s, 1H), 8.15(d, 1H) | | Meth 39 |
| 54 | 2-Amino-4-(1-cyclopropylmethyl-2-methylimidazol-5-yl)pyrimidine | 0.35(m, 2H), 0.53(m, 2H), 1.25(m, 1H), 2.50(s, 3H), 4.45(d, 2H), 5.00(brs, 2H), 6.85(d, 1H), 7.50(s, 1H), 8.25(d, 1H) | 230 | Meth 41 |
| 55 | 2-Amino-4-[1-(tetrahydrofur-3-yl)-2-methylimidazol-5-yl]pyrimidine | 2.11(m, 1H), 2.4-2.6(m, 4H), 3.68(q, 1H), 3.96(d, 2H), 4.17(m, 1H), 6.14(m, 1H), 6.58(brs, 2H), 6.79(d, 1H), 7.35(s, 1H), 8.15(d, 1H) | 246 | Meth 42 |
| 56 | 2-Amino-4-(1-cyclopropylmethyl-2-ethylimidazol-5-yl)pyrimidine | 0.03-0.00(m, 2H), 0.15-0.09(m, 2H), 0.89-0.80(m, 1H), 1.0(t, 3H), 2.49(q, 2H), 4.30(d, 2H), 6.26(s, 2H), 6.60(d, 1H), 7.23(s, 1H), 7.90(d, 1H) | 244 | Meth 43 |
| 57 | 2-Amino-4-[1-(1-cyclopropylethyl)-2-methylimidazol-5-yl]pyrimidine | 0.10(m, 1H), 0.34(m, 1H), 0.45(m, 1H), 0.65(m, 1H), 1.50(br s, 1H), 1.57(d, 3H), 2.5(s, 3H), 4.77(br s, 1H), 6.47(s, 2H), 6.77(d, 1H), 7.34(s, 1H), 8.13(d, 1H) | | Meth 44 |
| 58 | 2-Amino-4-[1-(1-cyclopropylethyl)-2-(methoxymethyl)imidazol-5-yl]pyrimidine | 0.10(m, 1H), 0.29(m, 1H), 0.37(m, 1H), 0.58(m, 1H), 1.57(m, 1H), 1.63(d, 3H), 3.25(s, 3H), 4.39(br s, 1H), 4.52(dd, 2H), 6.55(s, 2H), 6.82(d, 1H), 7.41(s, 1H), 8.17(d, 1H) | 274 | Meth 45 |
| 59 | 2-Amino-4-(1-methoxyisopropyl-2-ethylimidazol-5-yl)pyrimidine | 1.25(t, 3H), 1.45(d, 3H), 2.75(q, 2H), 3.15(s, 3H), 3.60(m, 1H), 3.92(m, 1H), 5.25(s, 1H), 6.50(s, 2H), 6.78(d, 1H), 7.37(s, 1H), 8.16(d, 1H) | 262 | Meth 48 |
| 60 | 2-Amino-4-(1-methoxyisopropyl-2-propylimidazol-5-yl)pyrimidine | 0.96(t, 3H), 1.46(d, 3H), 1.74(sext, 2H), 2.69(t, 2H), 3.16(s, 3H), 3.6(q, 1H), 3.94(t, 1H), 5.2(s, 1H), 6.5(s, 2H), 6.77(d, 1H), 7.36(s, 1H), 8.14(d, 1H) | 276 | Meth 49 |

Methods 62-65

The following compounds were prepared by the procedure of Method 61 using the appropriate starting materials.

| Meth | Compound | NMR | m/z | SM |
|---|---|---|---|---|
| 62 | 2-Anilino-4-(1-cyclpentyl-2-methylimidazol-5-yl)pyrimidine | (CDCl$_3$) 1.59(m, 2H), 1.85(m, 2H), 2.01(m, 4H), 2.57(s, 3H). 5.68(quintet, 1H), 6.90(d, 1H), 7.08(t, 1H), 7.26(s, 1H), 7.65(m, 3H), 7.57(d, 2H), 8.35(d, 1H) | 320 | Meth 40 |
| 63 | 2-Anilino-4-(1-cyclobutyl-2-methoxymethylimidazol-5-yl)pyrimidine | 1.64(m, 2H), 2.40(m, 4H), 3.30(s, 3H), 4.55(s, 2H), 5.47(quin, 1H), 6.98(t, 1H), 7.03(d, 1H), 7.28(t, 2H), 7.40(s, 1H), 7.71(d, 2H), 8.43(d, 1H), 9.51(s, 1H) | 336 | Meth 46 |
| 64 | 2-Anilino-4-(1-cyclopentyl-2-methoxymethylimidazol-5-yl)pyrimidine | 1.47(m, 2H), 1.69(m, 2H), 2.01(m, 4H), 3.29(s, 3H), 4.51(s, 2H), 5.51(m, 1H), 6.98(t, 1H), 7.04(d, 1H), 7.27(t, 2H), 7.43(s, 1H), 7.63(d, 2H), 8.44(d, 1H), 9.43(s, 1H) | 350 | Meth 47 |
| 65 | 2-Anilino-4-(1-cyclopropyl-2-methylimidazol-5-yl)pyrimidine | 0.67(m, 2H), 1.02(m, 2H), 2.43(s, 3H), 3.50(m, 1H), 6.91(t, 1H), 7.06(d, 1H), 7.26(t, 2H), 7.37(s, 1H), 7.78(d, 2H), 8.40(d, 1H), 9.46(s, 1H) | 292 | Meth 38 |

Method 66

N-(2-Methoxyethyl)-4-iodobenzenesulphonamide

A solution of 4-iodophenylsulphonyl chloride (3.64 g, 12 mmol) in DCM (30 ml) was added dropwise to a solution of 2-methoxyethylamine (1.3 ml, 15 mmol) and triethylamine (2 ml, 15 mmol) in DCM (60 ml) cooled by an ice bath to 0° C. The mixture was then allowed to warm to ambient temperature and stirred for 1 hour. The solvent was removed by evaporation and the resulting oil dissolved EtOAc (100 ml) and washed with 0.33 M aqueous citric acid solution (2×100 ml), brine (100 ml) and dried. The volatiles were removed by evaporation to give the title compound (4.1 g, 100%) as a clear oil. NMR 3.12 (2H, q), 3.28 (3H, s), 3.44 (2H, t), 4.90 (1H, t), 7.57 (2H, d), 7.81 (2H, d); m/z: 342.

Methods 67-74

The following compounds were synthesised in an analogous method to Method 66 using the appropriate starting materials.

| Ex | Compound | NMR | m/z |
|---|---|---|---|
| 67 | N-(Cyclopropylmethyl)-4-iodobenzenesulphonamide | 0.01(m, 2H), 0.32(m, 2H), 0.76(m, 1H), 2.60(t, 2H), 7.47(d, 2H), 7.72(t, 3H), 7.91(d, 2H) | 336 |
| 68 | N-(Tetrahydrofur-2-ylmethyl)-4-iodobenzenesulphonamide | 1.50(m, 1H), 1.80(m, 3H), 2.81(m, 1H), 3.10(m, 1H), 3.65(m, 2H), 3.84(m, 1H), 4.89(t, 1H), 7.49(d, 2H), 7.80(d, 2H) | 368 |
| 69 | N-(Pyrid-2-ylmethyl)-4-iodobenzenesulphonamide | 4.08(s, 2H), 7.21(m, 1H), 7.31(d, 1H), 7.51(m, 2H), 7.70(m, 1H), 7.91(m, 1H), 8.29(s, 1H), 8.40(d, 1H) | 375 |
| 70 | N-(Cyclobutyl)-4-iodobenzenesulphonamide | 1.45(m, 2H), 1.70(m, 2H), 1.90(m, 2H), 3.58(m, 1H), 7.52(d, 2H), 7.95(m, 3H) | 336 |
| 71 | N-(2-Trifluoroethyl)-4-iodobenzenesulphonamide | 3.69(q, 2H), 7.58(d, 2H), 7.93(d, 2H), 8.65(brs, 1H) | 364 (M − H)⁻ |
| 72 | N-(2-Ethoxyethyl)-4-iodobenzenesulphonamide | 1.01(t, 3H), 2.89(q, 2H), 3.30(m, 4H), 7.53(d, 2H), 7.75(t, 1H), 7.97(d, 2H) | 354 (M − H)⁻ |
| 73 | N-(t-Butyl)-4-iodobenzenesulphonamide | 1.10(s, 9H), 7.56(m, 3H), 7.95(d, 2H) | 338 (M − H)⁻ |
| 74 | N-(Cyclopropyl)-4-iodobenzenesulphonamide | 0.60(d, 4H), 2.27(m, 1H), 4.85(s, 1H), 7.60(d, 2H), 7.90(d, 2H) | 322 (M − H)⁻ |

Method 75

N-(2-Methoxyethyl)-N-(t-butyl)-4-iodobenzene-sulphonamide

Sodium hydride (71 mg, 1.77 mg) was added to a solution of N-t-butyl-4-iodobenzenesulphonamide (Method 73; 500 mg, 1.47 mmol), in anhydrous DMF (15 ml), under nitrogen at 0° C. The resulting suspension was stirred at 0° C. for 30 minutes. A solution of 1-bromo-2-methoxyethane (167 µl, 1.77 mmol), and sodium iodide (265 mg, 1.77 mmol) in DMF (15 ml) (which had been pre-stirred at ambient temperature for 1 hour), was then added dropwise to the mixture so that the reaction temperature was maintained at 0° C. and the mixture then stirred for 10 minutes. The mixture was allowed to warm to ambient temperature, and then heated at 60° C. for 20 hours and then allowed to cool to ambient temperature. A further solution of 1-bromo-2-methoxyethane (167 µl, 1.77 mmol), and sodium iodide (265 mg, 1.77 mmol), in DMF (15 ml), (pre-stirred at ambient temperature for 1 hour), was then added dropwise and the reaction mixture was heated at 60° C. for a further 20 hours. The mixture was then cooled and solvent removed by evaporation. The residue was dissolved in ether (25 ml), washed with 10% aqueous sodium hydroxide solution (20 ml), water (3×25 ml), and dried. The volatiles were removed by evaporation and the residue purified by flash chromatography on silica gel eluting with DCM to yield the title compound (147 mg, 25%), as a clear oil that crystallised on standing. NMR: 1.23 (s, 9H), 3.24 (s, 3H), 3.48 (s, 4H), 7.57 (d, 2H), 7.94 (d, 2H).

Method 76

4-(1-Cyclopronylmethyl-2-ethylimidazol-5-yl)-2-{4-[N-(2-methoxyethyl)-N-(t-butyl) sulphamoyl] anilino}pyrimidine 2-Amino-4-(1-cyclopropylmethyl-2-ethylimidazol-5-yl) pyrimidine (Method 56; 2.35 g, 9.67 mmol) was treated with N-(2-methoxyethyl)-N-(t-butyl)-4-iodobenzene sulphonamide (Method 75; 4.61 g, 11.6 mmol) under the conditions described in Example 22 to give the title compound (3.7 g, 75%). NMR: 0.0-0.02 (m, 2H), 0.07-0.10 (m, 2H), 0.89-0.95 (m, 1H), 1.09 (s, 9H), 1.15 (t, 3H), 2.60 (q, 2H), 3.17 (s, 3H), 3.36-3.41 (m, 4H), 4.42 (d, 2H), 7.10 (d, 1H), 7.55-7.60 (m, 3H), 7.77 (d, 2H), 8.30 (d, 1H), 9.89 (s, 1H). m/z 513.

Method 77

5-Acetyl-1-benzyl-2-methylimidazole

A crude mixture of 4-acetyl-1-benzyl-2-methyliridazole and 5-acetyl-1-benzyl-2-methylimidazole (Method 8 of WO 02/20512; 20 g, 93.5 mmol) was dissolved in isopropanol (200 ml) and cyclohexene (100 ml) and 10% palladium-on-carbon catalyst (20 g) added. The mixture was heated to reflux under a nitrogen atmosphere for two hours, then allowed to cool, the catalyst removed by filtration and the filtrate evaporated. The residue which contained title compound and 4-acetyl-2-methylimidazole was purified by chromatography on silica eluting with DCM/7N methanolic ammonia (99.5: 0.5 increasing in polarity to 94:6) to give the title compound (2.72 g). NMR: 2.26 (s, 3H), 2.37 (s, 3H), 5.56 (s, 2H), 6.95-6.98 (m, 2H), 7.20-7.32 (m, 3H), 7.92 (s, 1H).

Method 78

4-(1-Cyclopropylmethyl-2-methylimidazol-5-yl)-2-{4-[N-(2-methoxyethyl)-N-(t-butyl)sulphamoyl] anilino}pyrimidine 2-Amino-4-(1-cyclopropylmethyl-2-methylimidazol-5-yl)pyrimidine (Method 54; 2 g, 8.73 mmol) was treated with N-(2-methoxyethyl)-N-(t-butyl)-4-iodobenzenesulphonamide (Method 77; 3.82 g, 9.61 mmol) under the conditions described in Example 22. The reaction was quenched by the addition of acetic acid (250 µl, 4.37 mmol), the mixture was poured into water and extracted with EtOAc. The extracts were combined, washed with water and then brine, dried and the solvent removed by evaporation. The residue was purified by chromatography on silica gel eluting with DCM/MeOH (97:3) to give the title compound (1.4 g, 32%) as a pale yellow foam. NMR: 0.01 (m, 2H) 0.18 (m, 2H) 1.90 (m, H) 2.26 (s, 3H) 3.15 (s, 3H) 3.37 (m, 4H) 4.42 (d, 2H) 7.08 (d, H) 7.52 (s, H) 7.58 (d, 2H) 7.75 (d, 2H) 8.30 (d, H) 9.75 (s, H); m/z 499.

Method 79

4-(1-Cyclopropylmethyl-2-(2-hydroxy-2-methylpropyl)imidazol-5-yl)-2-{4-[N-(2-methoxyethyl)-N-(t-butyl)sulphamoyl]anilino}pyrimidine 4-(1-Cyclopropylmethyl-2-methylimidazol-5-yl)-2-{4-[N-(2-methoxyethyl)-N-(t-butyl)sulphamoyl] anilino}pyrimidine (Method 78; 1.15 g, 2.31 mmol) was dissolved in anhydrous THF (80 ml), under nitrogen. The solution was cooled to −78° C. and n-butyl lithium (2.88 ml of a 1.6 N solution in hexanes, 4.62 mmol), was added slowly, maintaining the temperature at less than −65° C. The reaction mixture was then stirred at −78° C. for 30 minutes, then acetone (1187 µl, 2.54 mmol) was added and mixture allowed to warm to ambient temperature and stirred for 1 hour. The reaction mixture was then poured into water (100 ml), and extracted with EtOAc (2×50 ml). The organic extracts were combined, washed with water (50 ml), brine (50 ml), and dried. The volatiles were removed and the residue was purified by chromatography on silica gel eluting with EtOAc to give the title compound (465 mg, 36%) as a yellow solid. NMR: 0.10 (m, 2H) 0.18 (m, 2H) 0.89 (m, H) 1.07 (s, 6H) 1.12 (s, 9H) 2.75 (s, 2H) 3.15 (s, 3H) 3.38 (m, 4H) 4.54 (d, 2H) 7.11 (d, H) 7.58 (m, 3H) 7.75 (d, 2H) 8.34 (d, H) 9.8 (s, H); m/z 557.

Method 80

4-(1-Cyclopropylmethyl-2-(2-methylprop-1-enyl) imidazol-5-yl)-2-{4-[N-(2-methoxyethyl-N-(t-butyl) sulphamoyl]anilino}pyrimidine Triethylamine (660 µl, 4.74 mmol) and methane sulphonyl chloride (248 µl, 3.30 mmol) were added to solution of 4-(1-cyclopropylmethyl-2-(2-hydroxy-2-methylpropyl)imidazol-5-yl)-2-{4-[N-(2-methoxyethyl)-N-(t-butyl)sulphamoyl] anilino}pyrimidine (Method 79; 440 mg, 0.791 mmol) in DCM (15 ml) and the mixture stirred at ambient temperature for 18 hours. The reaction mixture was washed with water (2×20 ml), brine (10 ml), dried and volatiles removed by evaporation. The residue was purification by chromatography on silica gel eluting with EtOAc/isohexane (60:40 increasing in polarity to 90:10) to give title compound (117 mg, 27%) as a pale yellow foam. NMR: 0.15 (m, 2H) 0.30 (m, 2H) 1.0 (m, H) 1.23 (s, 9H) 1.95 (s, 3H) 2.15 (s, 3H) 3.30 (hidden, 3H) 3.50 (m, 4H) 4.65 (d, 2H) 6.28 (s, H) 7.27(d, H) 7.71 (d, 2H) 7.83 (s, H) 7.88 (d, H) 8.43 (d, H); m/z 540.

Example 51

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)-(c) may be enteric coated by conventional means, for example to provide a coating of cellulose acetate phthalate.

The invention claimed is:
1. A compound of formula (I):

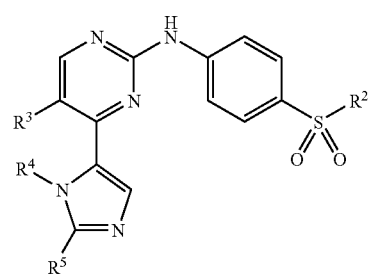

(I)

wherein:
$R^2$ is amino, $R^6$ or $R^6$—NH—;
$R^3$ is hydrogen, halo or cyano;
$R^4$ is $C_{3-6}$cycloalkyl, $C_{3-6}$cycloalkyl$C_{1-4}$alkyl, or heterocyclyl;
$R^5$ is $C_{1-6}$alkyl or $C_{2-6}$alkenyl; wherein $R^5$ may be optionally substituted on carbon by one or more methoxy; and
$R^6$ is $C_{1-4}$alkyl, $C_{2-4}$alkenyl, $C_{3-6}$cycloalkyl, $C_{3-6}$cycloalkyl$C_{1-3}$alkyl, or (heterocyclic group)$C_{1-3}$alkyl; wherein $R^6$ may be optionally substituted on carbon by one or more methoxy, ethoxy or trifluoromethyl;
or a pharmaceutically acceptable salt thereof.

2. The compound of formula (I) according to claim 1 wherein $R^2$ is $R^6$—NH— wherein $R^6$ is $C_{1-4}$alkyl, $C_{2-4}$alkenyl, $C_{3-6}$cycloalkyl, $C_{3-6}$cycloalkyl$C_{1-3}$alkyl or (heterocyclic group)$C_{1-3}$alkyl; and wherein $R^6$ may be optionally substituted on carbon by one methoxy, ethoxy or trifluoromethyl; or a pharmaceutically acceptable salt thereof.

3. The compound of formula (I) according to claim 1 wherein $R^3$ is hydrogen; or a pharmaceutically acceptable salt thereof.

4. The compound of formula (I) as claimed in claim 1 wherein:
$R^2$ is methylamino, allylamino, t-butylamino, 2-methoxyethylamino, 2-ethoxyethylamino, 3-methoxypropylamino, cyclopropylamino, cyclobutylamino, cyclopropylmethylamino, 2,2,2-trifluoroethylamino, tetrahydrofur-2-ylmethylamino or pyrid-2-ylmethylamino;
$R^3$ is hydrogen;
$R^4$ is cyclopropylmethyl, cyclobutyl, cyclopropyl, cyclopentyl or tetrahydrofur-3-yl; and
$R^5$ is methyl;
or a pharmaceutically acceptable salt thereof.

5. The compound of formula (I) as claimed in claim 1 selected from:
4-(1-cyclopentyl-2-methylimidazol-5-yl)-2-{4-[N-(cyclopropyl)sulphamoyl]anilino}pyrimidine;
4-(1-cyclopropylmethyl-2-methylimidazol-5-yl)-2-{4-[N-(2-methoxyethyl)sulphamoyl]anilino}pyrimidine;
4-(1-cyclopropylmethyl-2-methylimidazol-5-yl)-2-{4-[N-(2,2,2-trifluoroethyl)sulphamoyl] anilino}pyrimidine; and
4-(1-cyclopropylmethyl-2-methylimidazol-5-yl)-2-{4-[N-(cyclobutyl)sulphamoyl]anilino}pyrimidine;
or a pharmaceutically acceptable salt thereof.

6. The compound of formula (I) according to claim 1 wherein:
$R^3$ is hydrogen, chloro or fluoro;
$R^4$ is a heterocyclyl selected from tetrahydropyranyl and tetrahydrofuranyl;
$R^5$ is methyl; and
$R^6$ is $C_{1-4}$alkyl;
or a pharmaceutically acceptable salt thereof.

7. The compound of formula (I) according to claim 6 wherein $R^4$ is tetrahydropyranyl; or a pharmaceutically acceptable salt thereof.

8. The compound of formula (I) according to claim 1 wherein $R^5$ is $C_{1-6}$alkyl; or a pharmaceutically acceptable salt thereof.

9. The compound of formula (I) according to claim 8 wherein $R^5$ is methyl; or a pharmaceutically acceptable salt thereof.

10. A process for preparing a compound of formula (I) as claimed in claim 1 or a pharmaceutically acceptable salt thereof which process comprises:

Process a) reaction of a pyrimidine of formula (II):

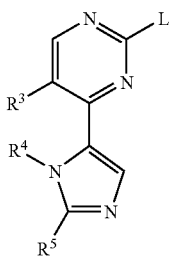

(II)

wherein L is a displaceable group; with an aniline of formula (III):

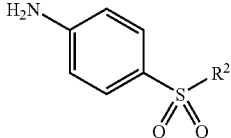

(III)

or
Process b) reacting a compound of formula (IV):

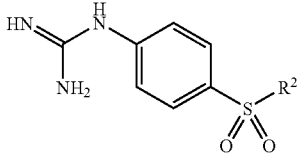

(IV)

with a compound of formula (V):

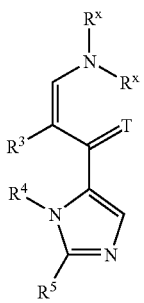

(V)

wherein T is O or S; $R^X$ may be the same or different and is $C_{1-6}$alkyl; or Process c) for compounds of formula (I) where $R^2$ is amino or a group $R^6$—NH—; reacting a pyrimidine of formula (VI):

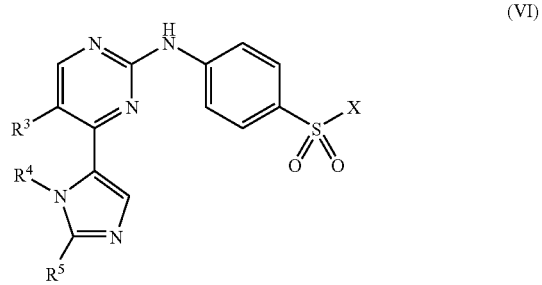

(VI)

wherein X is a displaceable group; with an amine of formula (VII):

$$R^a—NH_2 \qquad (VII)$$

wherein $R^a$ is hydrogen or $R^6$; or

Process d) reacting a pyrimidine of formula (VIII)

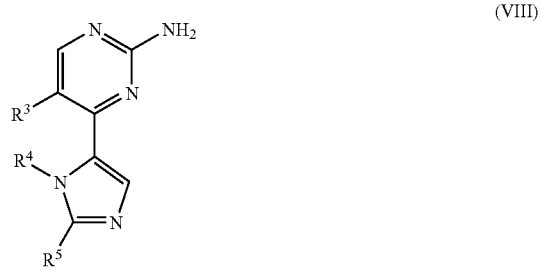

(VIII)

with a compound of formula (IX):

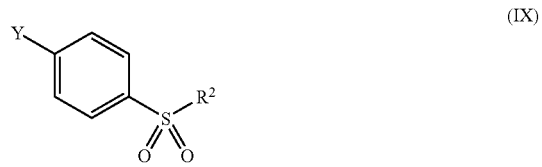

(IX)

where Y is a displaceable group;
and thereafter optionally:
  i) converting a compound of the formula (I) into another compound of the formula (I);
  ii) removing any protecting groups;
  iii) forming a pharmaceutically acceptable salt.

11. A pharmaceutical composition which comprises a compound of the formula (I), or a pharmaceutically acceptable salt thereof, according to any one of claims 1, 2, 3, 4, 5, 8, and 9, in association with a pharmaceutically-acceptable diluent or carrier.

12. A method for the treatment of rheumatoid arthritis, which method comprises administering to said animal an effective amount of a compound of the formula (I), or a pharmaceutically acceptable salt thereof, according to any one of claims 1, 2, 3, 4, 5, 8, and 9.

* * * * *